United States Patent [19]
van Krieken et al.

[11] Patent Number: 5,391,189
[45] Date of Patent: Feb. 21, 1995

[54] RATE ADAPTIVE DUAL CHAMBER PACING SYSTEM AND METHOD WITH AUTOMATIC ADJUSTMENT OF OPERATING PARAMETERS FOR MINIMIZING SENSOR-SINUS COMPETITION

[75] Inventors: Frits M. van Krieken; Gustaaf A. Stoop, both of Dieren; Johannes S. van der Veen, Arnhem, all of Netherlands

[73] Assignee: Vitatron Medical, B.V., Dieren, Netherlands

[21] Appl. No.: 147,347

[22] Filed: Nov. 4, 1993

[51] Int. Cl.⁶ .................................. A61N 1/365
[52] U.S. Cl. ............................................ 607/17
[58] Field of Search ........................................ 128/17

[56] References Cited

U.S. PATENT DOCUMENTS

| | | | |
|---|---|---|---|
| 4,527,568 | 7/1985 | Rickards | 128/419 PG |
| 4,856,523 | 8/1989 | Sholder et al. | 128/419 PG |
| 5,065,759 | 11/1991 | Begemann et al. | 128/419 PG |
| 5,144,949 | 9/1992 | Olson | 128/419 PG |
| 5,247,930 | 9/1993 | Begemann et al. | 607/11 |

FOREIGN PATENT DOCUMENTS

0326629A1  2/1988  European Pat. Off.

*Primary Examiner*—William E. Kamm
*Attorney, Agent, or Firm*—Woodcock Washburn Kurtz Mackiewicz & Norris

[57] ABSTRACT

There is disclosed a pacemaker, a dual chamber VDD(R) or DDD(R) pacemaker, having improved features for avoiding undesired sensor-sinus competition and providing blended sensor and sinus (atrial) control. The pacemaker employs atrial hysteresis which is used during sensing of natural atrial beats in order to enable tracking the sinus signals that occur at rates below the current pacing limit; and sensor hysteresis which prevents early takeover by sensor control and, in a DDDR pacer, controls when the sensor rate controls over a sensed sinus rate and also enables dropping the pacing rate during sensor control so as to enable finding and tracking of underlying lower rate sinus signals. The sensor hysteresis function is automatically adapted by obtaining and processing scattergram data representative of the sensor rate compared to the average of the natural sinus rate, and adjusting the sensor hysteresis function to optimally match the data. The atrial hysteresis function is also automatically adjusted as a function of rate by obtaining and processing scattergram data representative of sinus jitter, i.e., the difference between the current rate of the last atrial interval and the average sinus rate. In addition, blending of sensor and sinus control is achieved by automatic adjustment of the rate response curve based on accumulated data representative of RR signals as a function of running atrial rate.

51 Claims, 14 Drawing Sheets

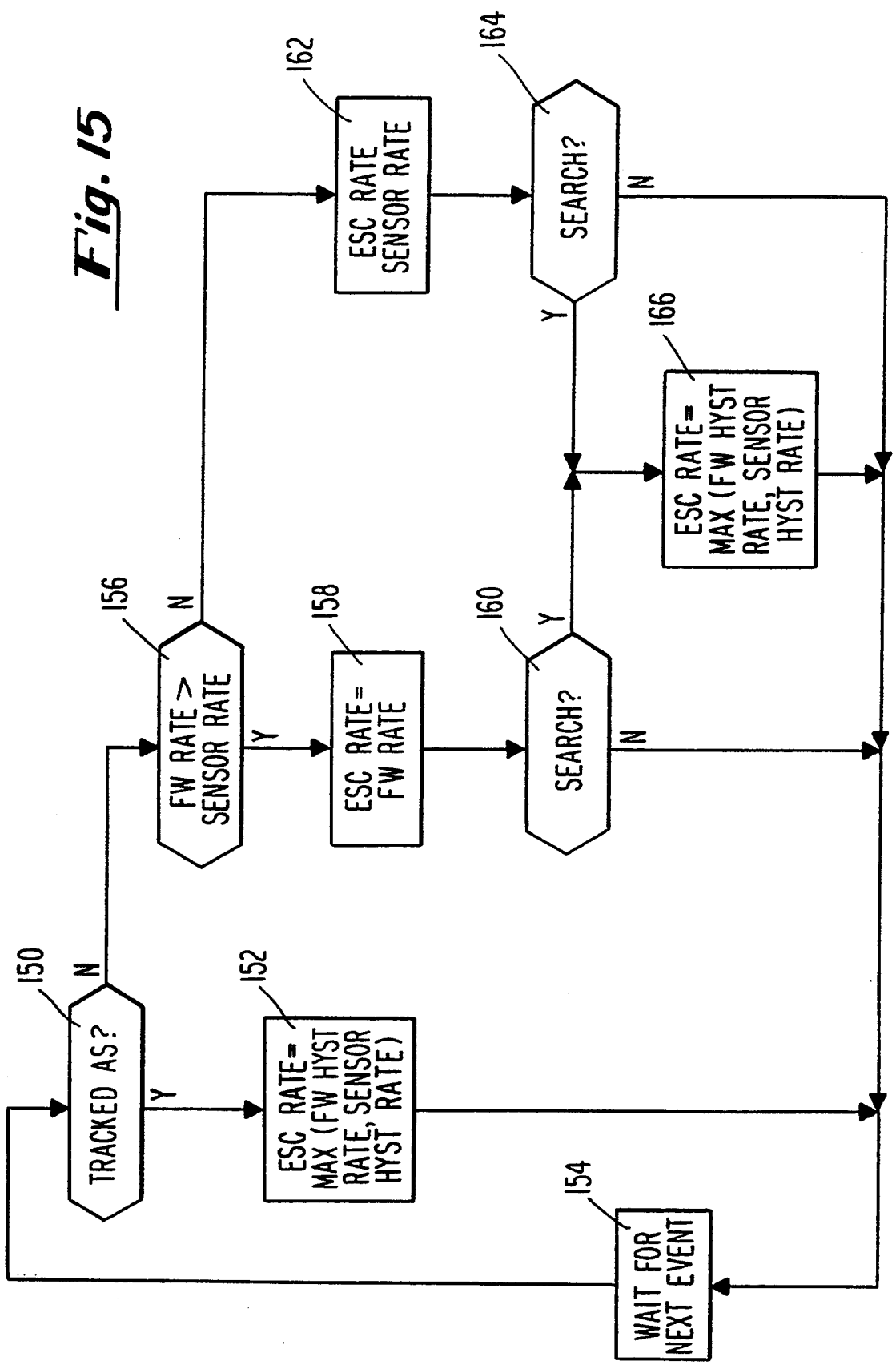

RATE ADAPTIVE DUAL CHAMBER PACING SYSTEM AND METHOD WITH AUTOMATIC ADJUSTMENT OF OPERATING PARAMETERS FOR MINIMIZING SENSOR-SINUS COMPETITION

FIELD OF THE INVENTION

This invention lies in the area of rate-responsive cardiac pacemakers and the method of operation of same and, more particularly, dual chamber rate responsive pacemaker systems having blended sinus and sensor control so as to optimize tracking of a reliable simms rate while permitting sensor control where atrial signals are non-physiological or otherwise unreliable.

DESCRIPTION OF THE PRIOR ART

Dual chamber rate responsive pacemakers are now widely available from pacemaker manufacturers. Such pacemakers may be of many types, including the types designated as DDDR or VDDR. The DDDR pacemaker paces and senses in both chambers, i.e., both the atrium and the ventricle, and has rate responsive (RR) backup to provide pacing in the absence of sensed natural beats, or to provide rate responsive ventricular pacing during atrial tachyarrhythmias in the absence of natural ventricular beats. The DDDR pacemaker has a lead that is placed within the atrium to deliver atrial pace pulses, as well as to sense natural atrial (sinus) signals, ani a ventricular lead for pacing and sensing in the ventricle. In contrast, the VDDR pacemaker paces only in the ventricle, although it senses in both the atrium and the ventricle. The VDDR pacemaker system may be made simpler by incorporating a single lead, which has a floating atrial electrode for sensing atrial signals, in a known manner. The VDDR pacemaker is indicated for patients who are determined to have a good and reliable sinus rate, so that for a good bit of the anticipated lifetime of the patient, natural atrial signals will be present from which ventricular pace pulses can be tracked, thereby providing synchronized pacing.

For DDDR and VDDR pacemakers, there is an inherent desirability of maximizing use of the sinus rate, i.e., avoiding takeover of the pacing function as long as a good atrial signal is present and sensed. For a rate responsive pacemaker, this leads to the desirability of correlating the rate response as closely as possible to the sensed natural sinus, while still enabling the rate response to take over pacing control when and if the sinus does not accurately reflect cardiac demand. Thus, for example, if a patient develops chronotropic incompetence after implant of a VDDR pacemaker, there must be an ability to switch modes or otherwise enable the sensor response to override the sinus.

The prior art indicates many schemes for adjusting rate response as a function of exercise. Such schemes include algorithms for ramping up rate upon the onset of exercise, and ramping down rate after exercise, so as to provide a more physiologically natural response to exercise. Such pacemaker systems thus involve predetermined programming for optimizing the pacing response in terms of known optimum responses to exercise. It is also known to adjust the rate response as a function of a separate sensor, and to switch to the rate response mode if the atrial rate looks to be unreliable. See, for example, U.S. Pat. No. 4,527,568, Rickards, assigned to the same assignee as this invention, where atrial and sensor rate are compared, and the sensor takes over if conditions indicate that this is desirable. However, in pacemakers to date, there is no capability of enabling the rate response function (or algorithm) to track or adapt to the actual sinus rate. For DDDR and VDDR mode pacers there is a need to provide a rate response control wherein the sensor-indicated pacing rate is correlated to and tracks just below the sinus rate whenever the sinus rate is reliable, so as to optimize sensing of the atrial rate and provide for pacing takeover only when the sinus is unreliable (e.g., atrial tachyarrhythmias) or missing. Stated in another manner, there is a need for improvement in avoiding competition between sinus and sensor signals that would cause the pacemaker to operate under sinus control when the sinus was unreliable, or under sensor control when the sinus was reliable but was overtaken by a too-aggressive sensor signal.

The prior art patent literature discloses a number of pacemakers having various features for automatic mode switching, or "blending" control between sensor and sinus signals. U.S. application Ser. No. 08/049,181, filed Apr. 19, 1993, assigned to the same assignee and incorporated herein by reference, discloses a rate-adaptive pacemaker with the capability of adjusting the sensors rate relation as a function of current sensed sinus rate. This pacemaker provides a rate response which is controlled to follow the sensed sinus rate, i.e., the correlation between the sensor-indicated pacing rate and the sensor input is automatically adjusted by ongoing comparisons of sinus rate and sensor rate. U.S. No. 4,527,568 discloses mode switching whereby the atrial and sensor rates are compared, and the sensor takes over if conditions warrant. In U.S. Pat. No. 5,052,338, parameters for the rate vs. sensor curve can be selected by the physician. While this provides for increased optimization of the sensor response, it does not address the problem of sinus-sensor competition.

U.S. Pat. No. 4,856,523 shows the related concepts of extending the pacing escape interval following natural beats by an amount which is related to the sensor rate, i.e., a sensor indicated hysteresis; and automatic mode switching at higher rates. EPO application 0 326 629 shows a hysteresis interval in a rate-responsive pacer, where the hysteresis is a function of the variable basic escape interval, or pacing rate. While the prior art thus shows different hysteresis arrangements for dual chamber pacers, it does not suggest a second hysteresis applied to the sensor rate, i.e., "sensor hysteresis", that is variable as a function of rate and utilized together with a hysteresis applied to the sensed is rate so as to avoid sensor-sinus competition.

In view of the above review of the prior art, it is seen that there is a need for an improved rate adaptive dual chamber pacing system which optimizes sinus control as long as the sinus is reliable and which automatically adapts sensor-control pacing so as to minimize competition between pacing and any underlying sinus beat. Such a pacemaker evaluates the sensor rate in view of the sinus rate and provides optimized dual hysteresis functions following both atrial sense and atrial pace eventis.

SUMMARY OF THE INVENTION

In view of the above object of minimizing sensor-sinus competition, there is provided a dual chamber, rate adaptive pacing system and method wherein sinus and sensor data is collected and utilized for automatic adaption of the sensor vs. pacing rate function; adaptation of a sensor hysteresis which is operative to modify a sensor-determined rate; and adaptation of a flywheel hysteresis operative to modify a flywheel rate which follows sensed atrial signals. The pacemaker compiles scattergram data of two different varieties. The pacemaker accumulates a first set of data derived from atrial senses and the RR signals, representing the rate responsive signal (RR) and a measure of sensed atrial rate for each stable atrial beat over the range of the sensor function. A second scattergram-type compilation of data comprises data representative of the difference between the running atrial rate, or average atrial rate, and current atrial rate derived from the latest sensed atrial beat. The first set of data is used for comparison with the curvilinear sensor function and for adjusting of such sensor function over the pacing rate range so that the RR curve more accurately tracks reliable sinus rates. The first compilation of data is also used for generating a sensor hysteresis function operative over the pacing rate range which is used to control the rate of generated pace pulses at a hysteresis differential rate below the sensor-controlled rate. The data representative of the difference between running atrial rate and the current atrial rate represents sinus jitter, and is used for adjusting the flywheel distance (FWd) which normally sets the escape interval during tracking of sensed atrial beats.

BRIEF DESCRIPTION OF THE DRAWINGS

FIG. 15 is a flow diagram illustrating how the pacemaker of this invention sets the escape interval in accordance with the different hysteresis functions that may be enabled.

DESCRIPTION OF THE PREFERRED EMBODIMENTS

Figure 1:
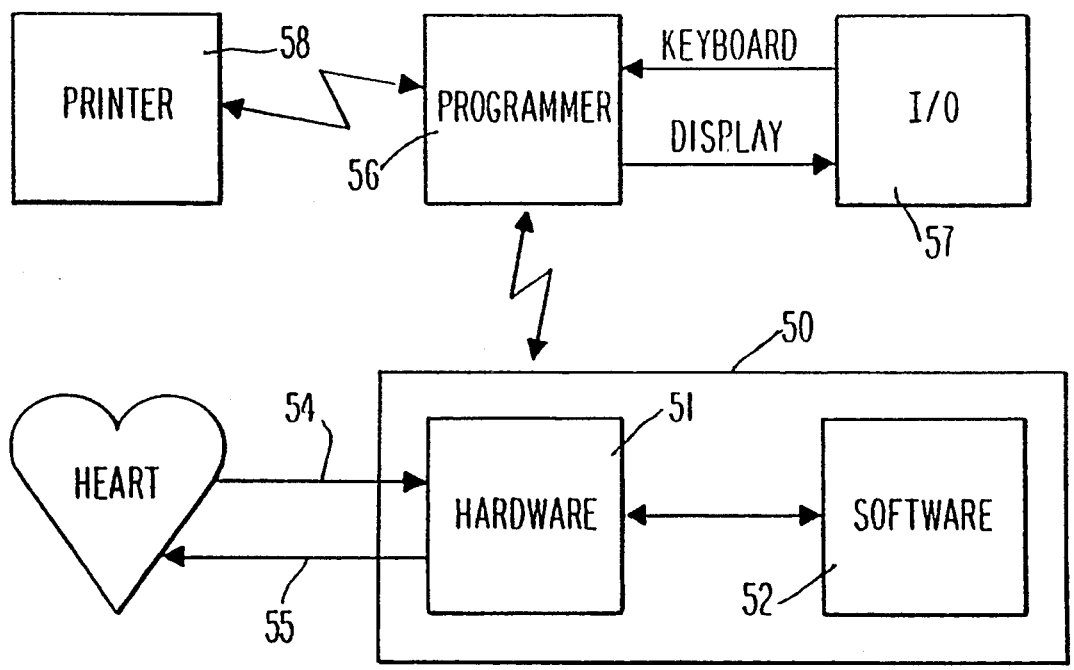
FIG. 1 is a block diagram of the overall pacing system of the invention, showing the environment in which the pacemaker software operates.

In the detailed description of the pacing system of this invention, as well as the illustrative figures, the following acronyms, abbreviations and symbols are utilized:

| Symbol | Definition |
|---|---|
| DPL | Dynamic Pacing Limit |
| LPL | Lower Pacing Limit |
| UPL | Upper Pacing Limit |
| LRL | Lower Rate Limit |
| URL | Upper Rate Limit |
| bpm | Beats Per Minute |
| DTL | Dynamic Tracking Limit |
| UTL | Upper Tracking Limit |
| WB | Wenckebach |
| NAB | No Atrial Blanked |
| PAC | Premature Atrial Contraction |
| TAS | Tachy Atrial Sense |
| DWL | Dynamic Wenckebach Limit |
| RR | Sensor-indicated rate signal derived from the sensor signal; RR function, or curve, varies with the sensor signal |
| $S_{avg}$ | Running average of the natural sinus rate. This can be any measure of the recent atrial rate, and can be the phys rate as defined in referenced U.S. Pat. No. 5,247,930 |
| s | Current sinus rate (A-A interval) |
| RR Hyst | Sensor Hysteresis |
| FWd | Flywheel distance, or distance between the current sinus rate or phys rate and the dynamic pacing limit. |
| FW Hyst | Flywheel Hysteresis. This is further atrial hysteresis |

| Symbol | Definition |
|--------|------------|
|        | -continued |
|        | below DPL. |

As used in this application, the term "atrial hysteresis" means an extension of the escape interval that is timed out following an atrial sense. This is a conventional usage of the term "hysteresis" as it has been used in the pacemaker literature, although the manner of determining such atrial hysteresis in this invention is new and different. Atrial hysteresis may be composed of one or two components. A first component is what is here referred to as the flywheel distance (FWd), which is a rate differential subtracted from the current atrial rate. Atrial hysteresis may also, optionally, include "Flywheel hysteresis," e.g., a predetermined value which is also subtracted from the atrial rate (as illustrated in FIG. 4c). Thus, if both FWd and flywheel hysteresis are employed, the atrial hysteresis is computed by subtracting the FWd and atrial hysteresis values from the rate of sensed atrial beats. The term "sensor hysteresis," RR Hyst, indicates a hysteresis increment to be subtracted from the sensor-controlled pacing rate (or an interval to be added to the escape interval). The pacemaker of this invention utilizes unique combinations of these hysteresis functions in order to reduce sensor/sinus competition, and also provides new and improved methods of adjusting the hysteresis functions so that they are optimally adapted to the patient's underlying sinus (atrial) rate, to the extent that such sinus rate is reliable. In practice a hysteresis rate is available for use corresponding to each value of the sensor rate and flywheel rate, including the lower rate limit. This invention makes a selected hysteresis value available for all situations; the hysteresis value is adapted to the circumstances, e.g.; it is a function of the last event and rate.

The pacing system of this invention is preferably software-based, i.e., the software controls all functions through the hardware, as illustrated in FIG. 1. Referring specifically to FIG. 1, the pacemaker 50 is shown as having a component hardware portion 51 and a software portion 52, the two portions being interconnected. The software is parameter-driven, i.e., there are numerous parameters that control the pacing behavior, diagnostic functions, etc. The hardware is interconnected with the patient's heart by one or more electrodes 55, and one or more sensor connections 54. As is well understood in the art, for a dual chamber pacemaker, there are generally two leads, an atrial lead and a ventricular lead, each lead having at least one electrode, unipole or bipole, positioned in the heart. The line 54 is illustrated as leading to the heart, as in a QT-type sensor arrangement, but may be attached to the outside case of the pacemaker or may couple to any other available sensor for sensing body parameter information used in rate responsive pacing systems. Further, in the preferred embodiment of the pacing system of this invention, sensor link 54 may comprise a pair of sensors, e.g., QT plus activity, as set forth in U.S. Pat. No. 5,065,759, incorporated herein by reference.

As further illustrated in FIG. 1, the pacer 50 is in telemetric communication with a programmer 56. The user can select parameters and program them through programmer 56, and can also interrogate parameter and diagnostic data from the implanted pacemaker. Interrogated information from the pacer can be coupled by telemetry directly to a printer 58. Input/output devices 57 are used to input information by the user to the programmer, or to display information received by the programmer from the pacemaker.

Figure 2:
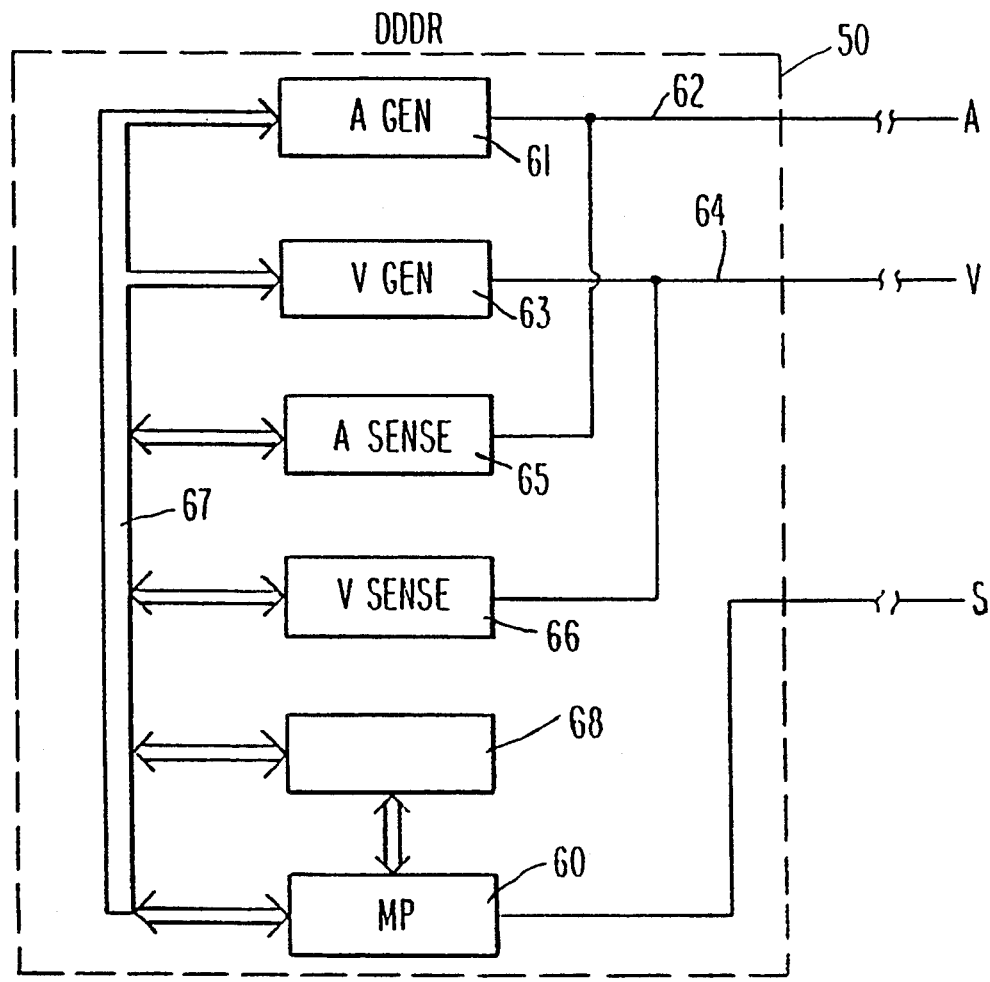
FIG. 2 is a block diagram which illustrates basic components of the pacemaker of this invention, together with leads and a sensor or sensors for delivering signals to and/or receiving signals from the patient.

Referring to FIG. 2, there is shown a basic block diagram of primary hardware components of a DDDR pacer 50. An atrial generator 61 is shown, having an output connected to lead 62 which communicates with the patient's atrium. An A sense amplifier 65 is illustrated also connected to atrial lead 62. A ventricular generator is illustrated which is connected to the patient's ventricle through lead 64. V sense amplifier 66 is also connected to lead 64, to receive and sense signals from the patient's ventricle. In one embodiment of this invention which preferably incorporates QT rate control, V sense block 66 also includes means for picking out and determining the timing of the evoked T wave. As is known, for a VDDR pacemaker, the A sense and V sense signals may come from the same lead. Generators 61 and 63 and sense blocks 65 and 66 are interconnected with microprocessor system 60, which microprocessor has software which is parameter-driven to control the operation of the hardware units. Microprocessor system 60 may be interconnected with hardware logic and/or timing circuits 68. The microprocessor system suitably consists of a D43 microprocessor with 4 k byte ROM and 624 bytes RAM (MC146805E2 compatible); and an M05 memory chip with 4 k byte ROM and 256 bytes RAM. It is preferred that the operating software fit in 8 k byte ROM, and have available for use 624 bytes of RAM; 256 bytes of RAM are held unused to enable future RAM routines (executable code located in RAM). In a manner well known in the art, the software contains a number of strategic places where escape points to a RAM routine are available. As affects the scope of this invention, the degree to which software supplants hardware, or vice versa, is a matter of design choice. Thus, for the many timing functions that are carried out in the pacing system of this invention, it is to be understood that the microprocessor may have built in timing circuits, or suitably may control external hardware timer circuits. Software control of pacing function is well known in the art, such that the following detailed discussions of the software specifications enable one of ordinary skill in this art area to design a system for carrying out the functions within the scope of the invention. Data inputted from programmer 56 is stored in memory associated with microprocessor.

Still referring to FIG. 2, there is shown a sensor S, indicated as providing an input to microprocessor system 60. Sensor S represents one or more sensors for monitoring one or more body parameters known to be indicative of desired pacing rate. Sensor S is illustrated as being outside the pacemaker, but may be physically located inside the pacemaker casing, as with certain activity sensors. Alternately, as is the case with the Q-T-type rate responsive pacemaker, the "sensor" information is actually obtained from the ventricular lead, by extracting timing information relating to the Q-T interval. As used in the practice of this invention, the term sensor or sensor signal may refer to information obtained from any available rate responsive sensor-type source. Also, as used in the claims hereto, the term "rate signal" may refer to a signal deriving its information from either or both a sensor source and the sensed atrial rate.

Figure 3:
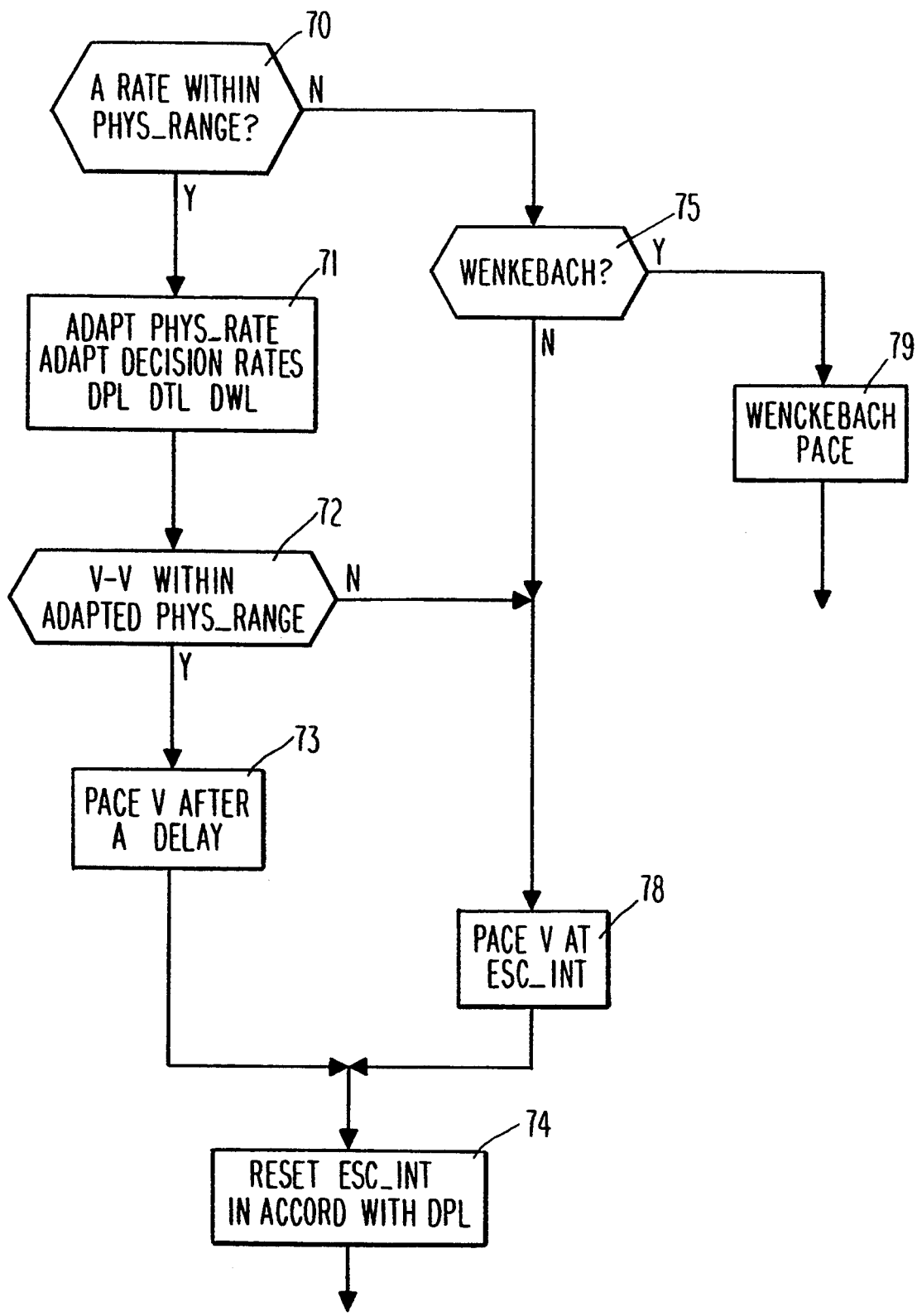
FIG. 3 is a simplified flow diagram illustrating dynamic AV tracking in a DDD or VDD mode.

Referring now to FIG. 3, there is shown a flow diagram illustrating procedure without hysteresis following an atrial event, and in particular illustrating tracking when an atrial event is determined to be physiological. This figure is presented as an example, to illustrate some of the terms and features utilized herein. See U.S. Pat. No. 5,241,930 incorporated by reference. At block 70, the software first determines whether an atrial rate(s) is within predetermined physrange limits. By atrial rate, reference is made to the rate corresponding to the A—A interval from the atrial event prior to the atrial event under examination. Thus, at block 70, the time interval from the prior atrial event is determined, and compared to a predetermined physrange, which range can be expressed either in terms of rate values or corresponding time intervals. The physrange limits comprise a lower limit referred to as dynamic pacing limit (DPL), which is a hysteresis type limit at which the pacer intervenes to pace, and an upper range limit referred to as dynamic tracking limit (DTL). The DTL determines how high an atrial rate can be tracked, while DPL sets the pacing interval, or rate, following a tine out due to no A sense. Also, the change of A rate is checked to see whether the change is physiologic.

If the A rate is within the physrange and change limits, the software branches to block 71, where the physrate is adapted as a function of the just determined atrial rate; also the decision rates which are coupled to the physrate are adapted, i.e., DPL, DTL and DWL are adapted. Phys-rate is a measure of the running average of the rate; when tracking it follows the atrial rate, and when pacing, it follows the pacing rate. See U.S. Pat. No. 5,247,930, incorporated herein by reference. It ms to be noted that the physrate and the decision rates can be adapted either before the start of or after the end of this routine. At 72 it is determined whether the synchronized ventricular pulse would have a rate within the adapted physrange, such that it can be tracked. Thus, the AV interval is added to the time of the atrial event, and the projected synchronous V stimulus time is compared with the prior V event to determine the V—V interval, and thus the V rate. Only if the determined V rate is within the adapted physiological range (DPL to DTL) does the software branch to block 73, to control the delivery of a ventricular pace after timeout of an AV-delay. If V—V is not within the physrange, the program branches to block 78.

Coming back to block 70, if the A rate is not within the physrange and rate change limits, the software branches to block 75, where it is determined whether the atrial event has fallen within a Wenckebach range. If yes, a Wenckebach pace is delivered as indicated at block 79, in accordance with predetermined Wenckebach criteria. If no, the program proceeds to block 78, where the ventricle is paced at the escapeinterval, which interval is normally set by the dynamic pacing limit. Following this, the escape interval is reset in accordance with DPL, as indicated at block 74.

Figure 4A:
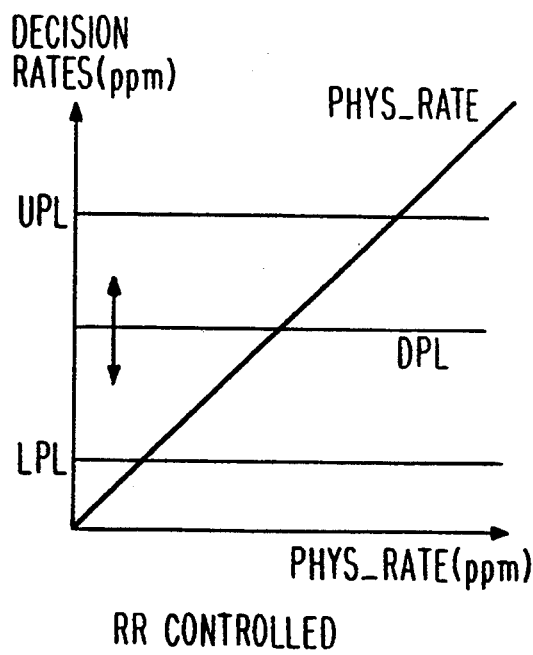
FIGS. 4a, 4b and 4c are curves illustrating the dynamic pacing limit (DPL) and the Flywheel Distance FWd, as used in the pacemaker of this invention.
Figure 4B:
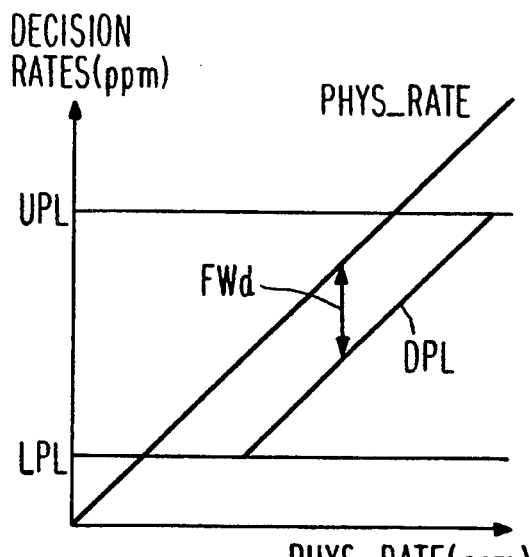
Figure 4C:
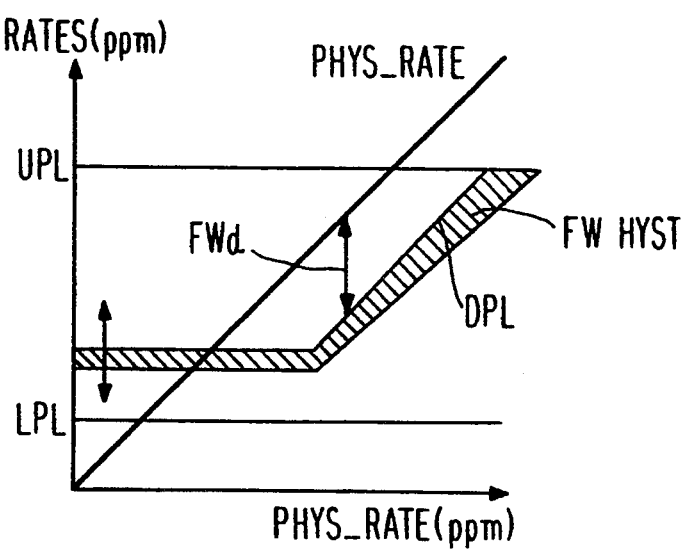

Referring to FIGS. 4a, 4b and 4c, the dynamic pacing limit is illustrated for the circumstances where it is RR controlled (FIG. 4a); "flywheel" controlled (FIG. 4b); and controlled by both RR and flywheel (FIG. 4c). In FIG. 4a, the dynamic pacing limit is shown as only RR controlled. As represented here, it is not a function of physrate, but for any given physrate may vary between programmable values of LPL and UPL as a function of the sensed parameter or parameters. In the FW controlled mode of FIG. 4b, DPL tracks the physrate, and thus the atrial rate, maintaining a distance FWd below the physrate as per conventional flywheel tracking arrangements. FWd is shown as a programmable distance. Note that DPL stays constant at LPL for all rates up to a rate corresponding to the lowest physrate where a flywheel window of FWd is established. In the situation where DPL is both RR and FW controlled, as illustrated in FIG. 4c, DPL can also be shifted up and down as a function of the sensor information, between the LPL and UPL limits. Indeed, the RR control, particularly without hysteresis, can override a physrate which reflects only A rate, for most of the range up to UPL. The shaded area below the DPL curve represents a form of atrial hysteresis, i.e., a band rates below DPL at which natural sinus beats can be sensed during non-pacing. This increases the area where tracking of the atrial rhythm is available. This feature may be particularly important in the RR mode, since it allows for some blending of the atrial and sensor influences. The availability of an atrial hysteresis means that the tracking mode can have more priority over the sensor.

Figure 5:
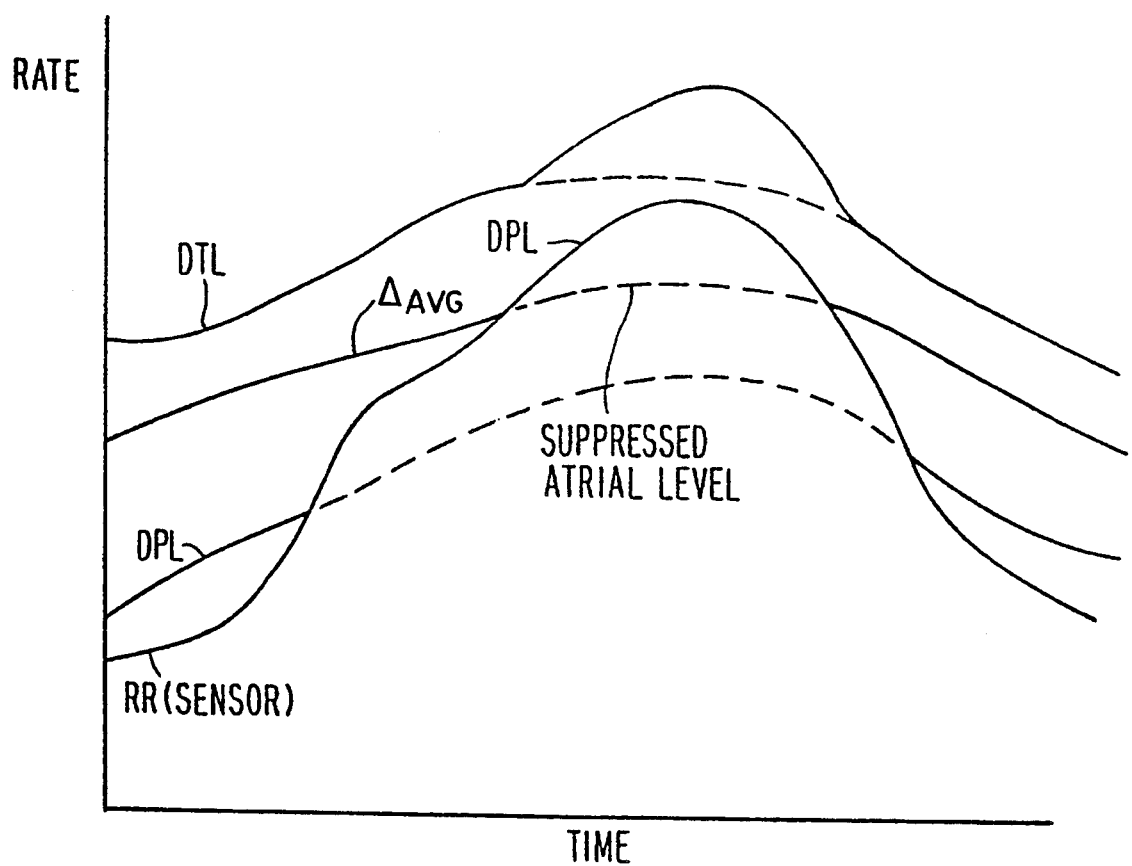
FIG. 5 is a graph illustrating how the sensor rate can control DPL and suppress the sinus (atrial) rate, in the absence of sensor hysteresis as employed in a preferred embodiment of this invention.

Referring now to FIG. 5, there is shown a time graph illustrating how the DPL and DTL decision rates can vary over time, as a function of either the sensed atrial (sinus) rate or the RR signal. This illustrates a pacemaker with dynamic decision curves, but without any sensor hysteresis. As seen, the RR signal can effectively take over DPL, such that DPL is not coupled to the physrate. Further, the RR signal can override physrate and cause a corresponding increase in DTL up to the programmed upper tracking limit (UTL) value.

Figure 6A:
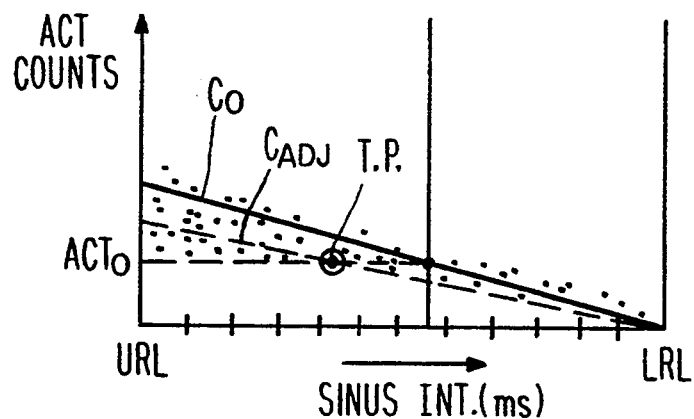
FIG. 6a is a scattergram showing data from which the pacemaker derives automatic adjustments of an activity sensor function curve in accordance with this invention.
Figure 6B:
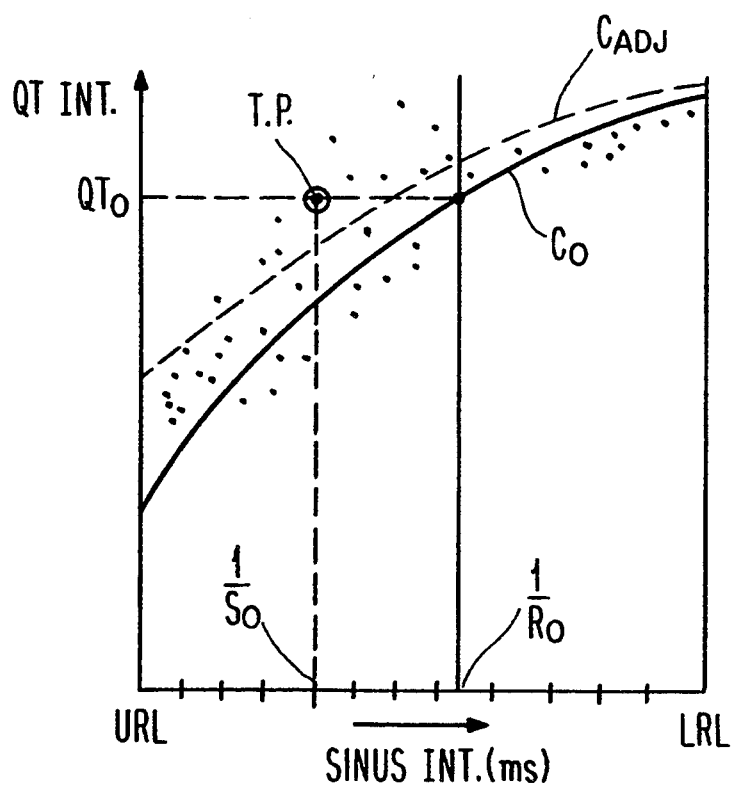
FIG. 6b is a scattergram showing data from which the pacemaker derives automatic adjustments of a Q-T sensor function curve in accordance with this invention.
Figure 6C:
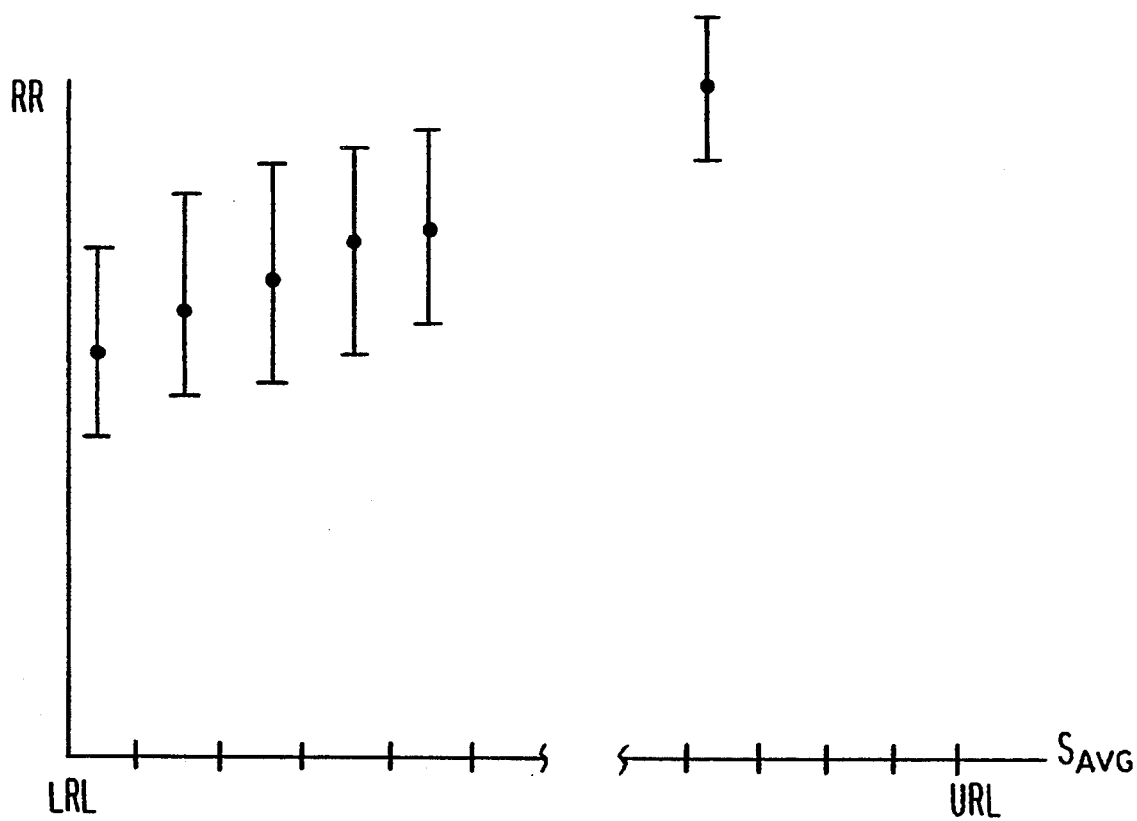
FIG. 6c is a graph illustrating the compilation of statistical data of (RR-s) obtained from the scattergram of FIG. 6a or FIG. 6b.

Referring now to FIGS. 6a, 6b, and 6c, there are presented illustrations of scattergrams and a method or organizing the scattergram data for automatically adjusting the RR function, or curve, in accordance with this invention. FIG. 6a shows an RR curve for an activity sensor, plotting ACT counts rs. average atrial interval in ms (the interval corresponding to $S_{avg}$ rate). The unadjusted curve is designated as $C_o$, and the dots represent periodic samples of activity count vs. average sinus rate. In this illustration the data indicate that the curve should be shifted so that the intersection with URL is lower. i.e., the curve should be shifted to a more aggressive slope. See referenced U.S. Pat. No. 5,065,759. For example, the data point indicated as T.P., for test point, corresponds to an ACT value of $ACT_o$ at an $S_{avg}$ interval which is less than what would be indicated by curve $C_o$, i.e., at a higher rate. The adjusted curve, shown as a dashed line and marked $C_{ADJ}$, more nearly fits the scattergram data. Note that a decision to adjust is not based on one test point; this is simply an illustration of the relation between the RR curve and the data. The same situation is illustrated in FIG. 6b, which plots QT interval vs. average atrial interval. Here again, the scattergram data shows that the curve is not sufficiently aggressive, particularly for higher rates (smaller intervals). For example, at the test point T.P., QT corresponds to an average sinus interval which is significantly less than that which would be indicated by the initial curve C0 (i.e., the data point is at a higher rate than would be indicated by the curve). Accordingly, the adjusted curve, $C_{adj}$, should be shifted upward for this sensor, toward the dashed line. Referring to FIG. 6c, there is shown a graph representing compilation of data as used in a preferred embodiment of this invention. In this curve, the sensor rate (RR) data is plotted against $S_{avg}$, the $S_{avg}$ axis being divided up into increments. Within each increment (or bin) of the range between LRL and URL, the data is compiled to indicate the MAX, MIN, and MEAN value of RR. This data in turn can then be used for determining the adjusted curve $C_{adj}$, e.g., by getting the value of $RR_{MEAN}-S_{avg}$, and fitting the curve.

Figure 7:
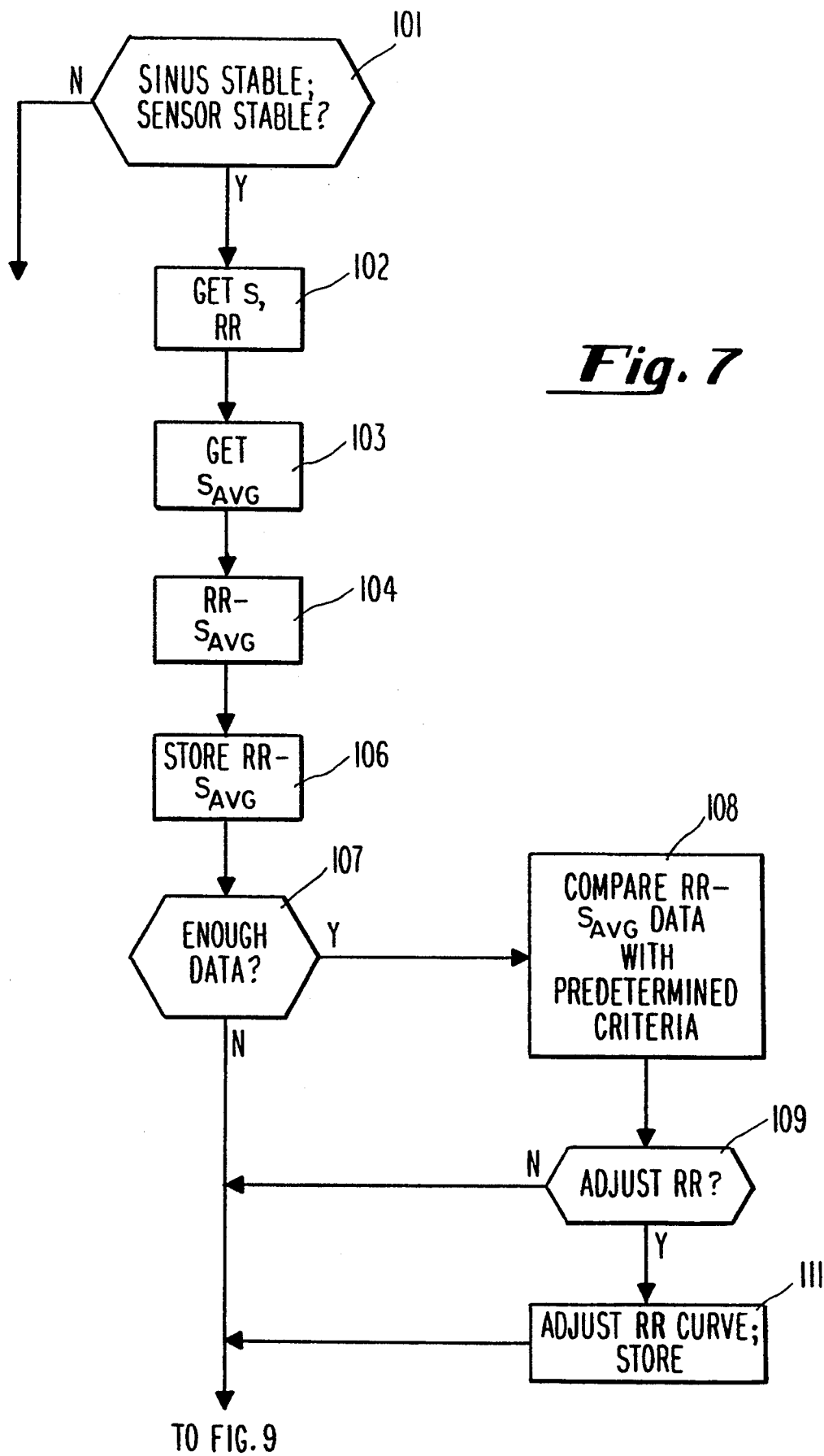
FIG. 7 is a flow diagram of logic steps taken in implementing automatic adjustment of the sensor function on the basis of the scattergram data such as illustrated in FIG. 6a or FIG. 6b.

Referring now to FIG. 7, there is shown a diagram for implementing automatic slope adjustment of the rate response curve in accordance with this invention. Although the flow diagram is drawn to represent software logic steps, it is to be understood in the art that the implementation can be embodied with any combination of hardware and software. This subroutine may suitably be entered following exit of the subroutine shown in FIG. 3. At step 101, it is determined whether the sinus rate is stable and whether the sensor is stable. For example, the data is not reliable around times of exercise, but is more reliable during moments of normal daily activity. A reasonable stability check is to determine whether the last n consecutive beats have been within a predetermined sub-range of rates, i.e., rate is not fluctuating greatly. If the data representing the difference between the sinus and the RR rate is not reliable, the routine exits. If the atrial signal and sensor are stable, then the routine proceeds to block 102. At block 102, the pacemaker gets the atrial rate s of the last interval, and the RR value. At block 103, the pacemaker determines a measure of the average atrial rate, $S_{avg}$. This may be the physrate as was discussed above, or may be any other measure of the average sinus rate, e.g., over a predetermined number of recent pacemaker cycles. At block 104, the pacemaker calculates $RR-S_{avg}$. Following this, at block 106, the recently calculated value of $RR-S_{avg}$ is stored. Such storage may be in any desired manner, e.g., the arrangement as set forth in FIG. 6a. At block 107, it is determined whether enough scattergram data has been collected, i.e., is there enough relevant data to be used for the purpose of adjusting the sensor curve? If not, the routine exits. If yes, the routine branches to 108 and analyses the data. This analysis may be carried out by comparing, at each of the range intervals as illustrated in FIG. 6c, the mean RR average with the stored RR value of the curve for the center of that range interval. Or, a mean value of $RR-S_{avg}$ can be computed for each sub-range value; if any one or more of such comparisons exceeds a predetermined threshold limit, then a decision is made at 109 to adjust the curve. It is to be appreciated that any statistical measures of deviation which warrant curve adjustment may be employed within the scope of this invention. If the decision to adjust is yes, the routine branches to block 111, anc the RR curve is adjusted and stored as the new RR curve in memory. The adjustment is suitably a curve-fitting adjustment, and may be implemented by adjusting the curve up or down by a predetermined unit of change at each range increment, in accordance with the comparison made in block 108.

It is to be understood that other equivalent ways of storing and processing the scattergram data are within the scope of the invention. Thus, as shown, the pacemaker may compute the $RR-S_{avg}$ data each pacemaker cycle that the routine is run; at block 106, the pacemaker can update the mean value of $RR-S_{avg}$ for each bin. Alternately, each cycle the pacemaker can simply store data representing RR signal values as a function of atrial rate, i.e., an RR value and its corresponding $S_{avg}$ value, and then compute the differences and means after a yes decision at 107.

In another feature of this invention for blending the sensor control with sinus control, a sensor hysteresis value "RR Hyst" is calculated; this value is subtracted from the RR value to obtain a rate which can be used to determine when the sensor can overtake the sinus, as discussed in connection with FIG. 15. The use of such a sensor hysteresis feature is an additional option which, when combined with the atrial, or "flywheel" hysteresis, permits more effective blending of RR operation and sinus tracking. The manner of selecting which hysteresis value is to be used, and when, is also discussed in connection with FIG. 15.

Figure 8A:
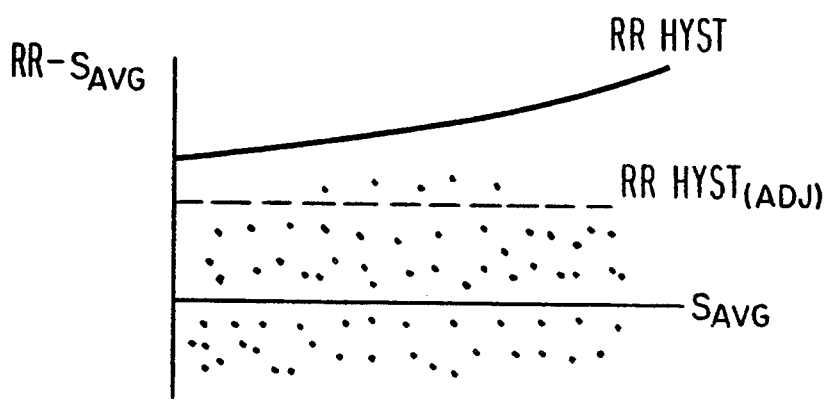
FIG. 8a is a scattergram graph of data representing the difference between the sensor-indicated rate and average sinus rate from which the sensor hysteresis function RR Hyst is determined.

Referring to FIG. 8a, there is shown a solid line indicted as RR Hyst plotted against average atrial rate. This curve represents an initial sensor hysteresis setting, yielding sensor hysteresis values as a function of atrial rate which as shown are initially higher than the expected chronic settings. In use, the RR Hyst value can be used in a DDDR pacer to set a hysteresis search depth when searching is done while pacing; and sensor hysteresis is used in both DDDR and VDDR pacers to prevent sensor takeover where RR-s is less than RR Hyst. Also indicated on FIG. 8a is scattergram data in the form of data points representing the difference between the sensor-indicated rate (RR) and the current average sinus rate ($RR-S_{avg}$). As illustrated in FIG. 8a, most of this scattergram data shows values of $RR-S_{avg}$ to have an absolute value less than the RR Hyst value for the corresponding average sinus rate. As long as this situation holds, RR Hyst may be periodically recalculated to drop the line one step across the rate range until very few or no data points end up above it, thereby optimizing the hysteresis value. Such an adjusted sensor line is shown as the dashed line at RR $Hyst_{(adj)}$. The scattergram data is obtained while pacing under sensor control ($RR-S_{avg}$ is positive) or tracking, where $RR-S_{avg}$ is nominally negative. To obtain data when $RR-S_{avg}$ is positive, a DDD pacemaker must periodically go into a hysteresis search mode, whereby the pacing rate is dropped for a predetermined number of cycles in order to look for an underlying sinus rhythm. See U.S. Pat. No. 3,921,642, incorporated herein by reference, for a discussion of rate searching.

Figure 8B:
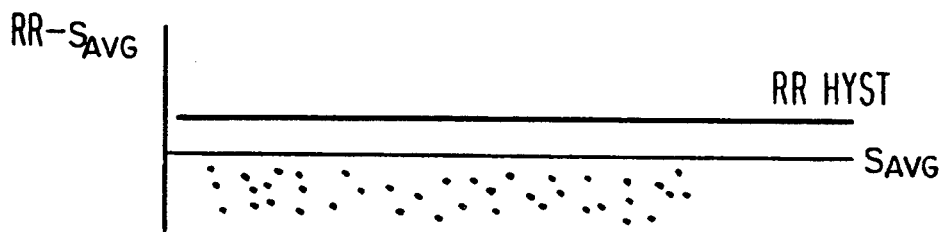
FIG. 8b illustrates a typical scattergram result where the sensor is not sufficiently aggressive.
Figure 8C:
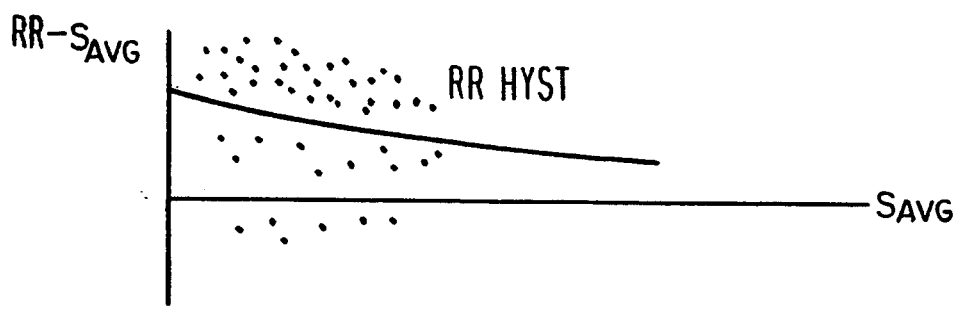
FIG. 8c illustrates a representative scattergram where the sensor is too aggressive.
Figure 8D:
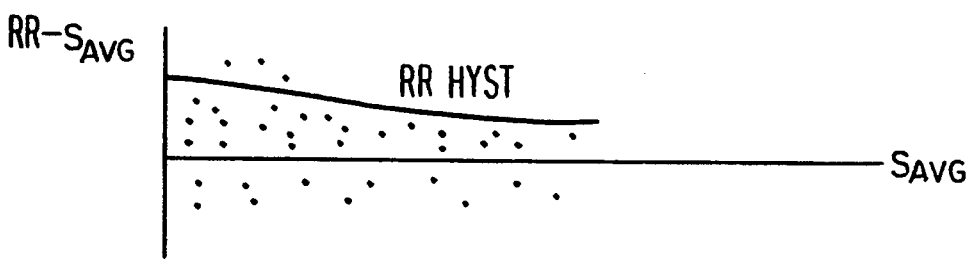
FIG. 8d represents a typical scattergram where the hysteresis function is adjusted to the scattergram data in an optimized manner.

Referring to FIG. 8b, there is shown a graph of scattergram data where the sensor is not sufficiently "aggressive", such that sensor hysteresis drops to and remains at a preset minimum, i.e., RR Hyst equals approximately 0. In FIG. 8c, there is illustrated the situation where the sensor is too aggressive, and the RR Hyst line must be pushed up periodically in order to make the effective sensor-controlled rate less aggressive. In FIG. 8d, there shown a histogram situation where RR Hyst is effectively optimized so that the sensor hysteresis curve is matched to the scattergram data, with very few data points above it. It also is to be recognized that the slope of RR Hyst may indicate that further correction of blending is required by adjusting of the RR curve.

Figure 9:
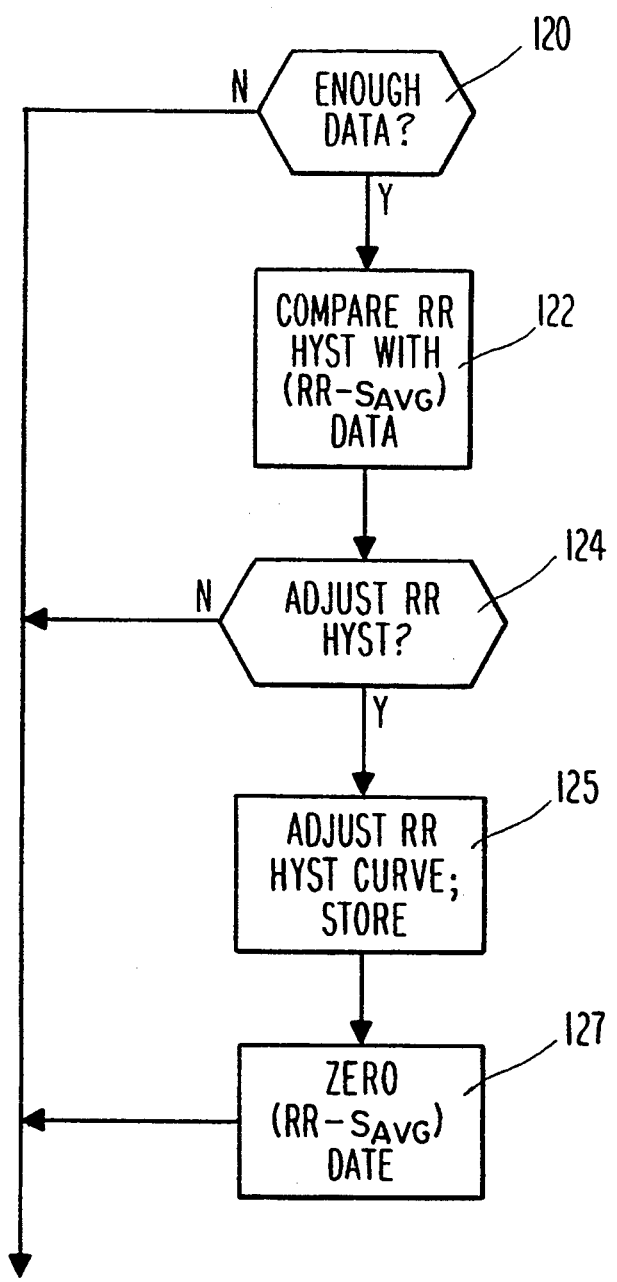
FIG. 9 is a flow diagram of the logic steps taken in determining sensor hysteresis scattergram data and in automatically adjusting the sensor hysteresis (RR Hyst) function.

Referring now to FIG. 9, there is illustrated a flow diagram of the logic steps in automatically adjusting the RR Hyst function. The routine of FIG. 9 is suitably entered following exit of the routine shown in FIG. 7. At block 120, it is determined whether sufficient scattergram data has been collected from which a reliable adjustment of the hysteresis curve can be made. If yes, the routine branches to block 122, where the stored RR Hyst curve is compared with the collected $RR-S_{avg}$ scattergram data. This comparison may be made in a manner similar to that discussed above for automatic adjustment of the RR curve. On the basis of this comparison, it is decided at 124 whether to adjust RR Hyst. If no, meaning that the RR Hyst curve is sufficiently well adjusted with respect to the scattergram data, the routine exits. However, is adjustment is called for, this is done at block 125, and the adjusted RR Hyst curve is stored in memory. Following this, at 127, the histogram data is zeroed out, or weighted so that the following data has more influence.

Figure 10A:
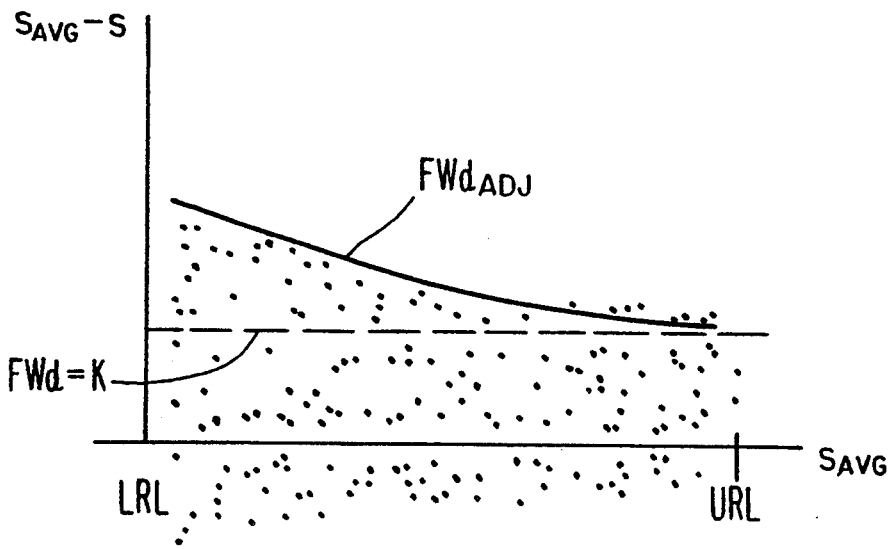
FIG. 10a is a typical scattergram showing atrial jitter representative of the difference between average sinus rate and current sinus rate, from which the FWd is determined.

Referring next to FIG. 10a, there is shown an illustration of a scattergram representing the "jitter" of the atrial rate, i.e., the difference between the current atrial rate of each cycle and the running average sinus rate ($S_{avg}$). As illustrated, the example shows data points showing a larger deviation toward the lower rates than toward the upper rate limit. The $S_{avg}$-s distance, when positive thus represents the distance below physrate that a sinus beat might be expected, and is an indication of what the FWd would optimally be. The solid line labelled $FWd_{adj}$ is drawn so that it substantially fits the upper extent of the data points, and represents a desired adjusted FWd curve. This is contrasted with the dashed line labelled FWd=K, where the flywheel distance is constant.

Figure 10B:
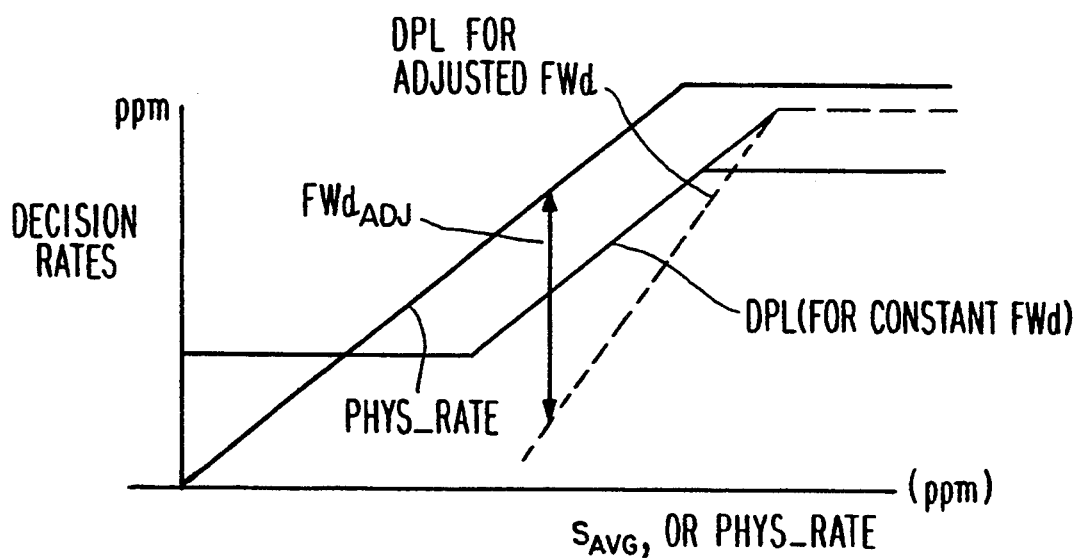
FIG. 10b is a graph illustrating how DPL is changed in accordance with the adjusted FWd.

Referring to FIG. 10b, the graph shows the dynamic pacing limit for a constant FWd, and the dashed line shows the dynamic pacing limit for an adjusted FWd corresponding to the curve in FIG. 10a. In this example, there is no additional hysteresis illustrated, i.e., the intervention pacing rate is phys-rate minus FWd. Note that the hysteresis effect provided by FWd is a function of rate, and is larger at lower rates.

Figure 11:
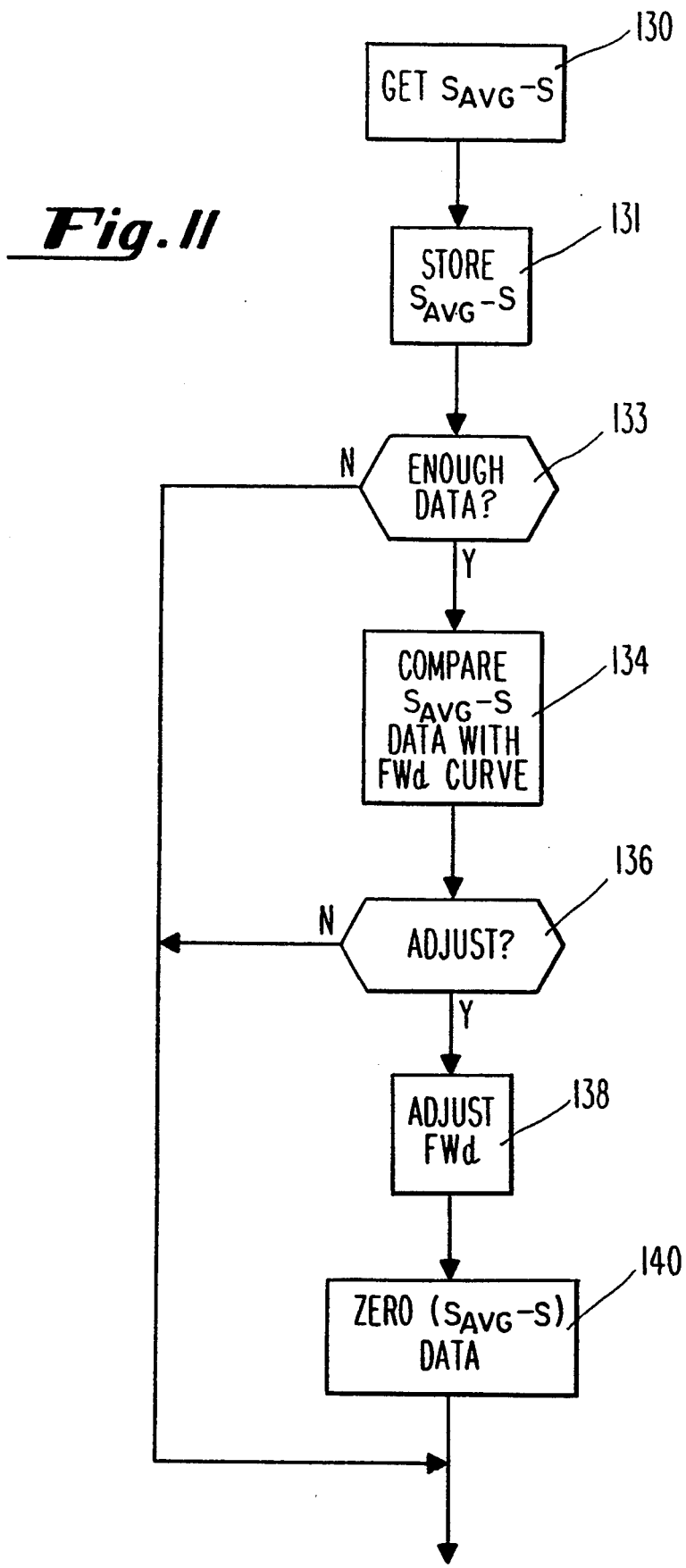
FIG. 11 is a flow diagram illustrating the logical steps taken by the pacemaker system of this invention for automatic adjustment of FWd.

Referring now to FIG. 11, there is shown a flow diagram for carrying out the logic steps of the embodiment of this invention comprising auto-adjust of the flywheel distance i.e., automatic adjustment of FWd so as to provide a variable DPL which is optimized to the sinus jitter. This portion of the routine may be entered from the exit of the routine shown in FIG. 9. At 130, the pacemaker obtains atrial rate s, which is the inverse of the A—A interval just completed. Following this, the determination of $S_{avg}$ - s is made, and this data is stored at block 131, thereby compiling the scattergram data. At 133, it is determined whether there is enough data to compare the sinus jitter data with the FWd curve. If no, the routine exits. If yes, it proceeds to 134 to make a comparison of the $S_{avg}$ - s data with the FWd curve which is stored in memory, in a manner such as discussed above at blocks 108 and 122. If the decision at 136 is not to adjust, the routine exits. If the decision is to adjust, the dynamic pacing limit (DPL) and FWd are adjusted as shown at block 138. Following this, the $S_{avg}$ - s data is zeroed at 140, and the routine exits.

Figure 12A:
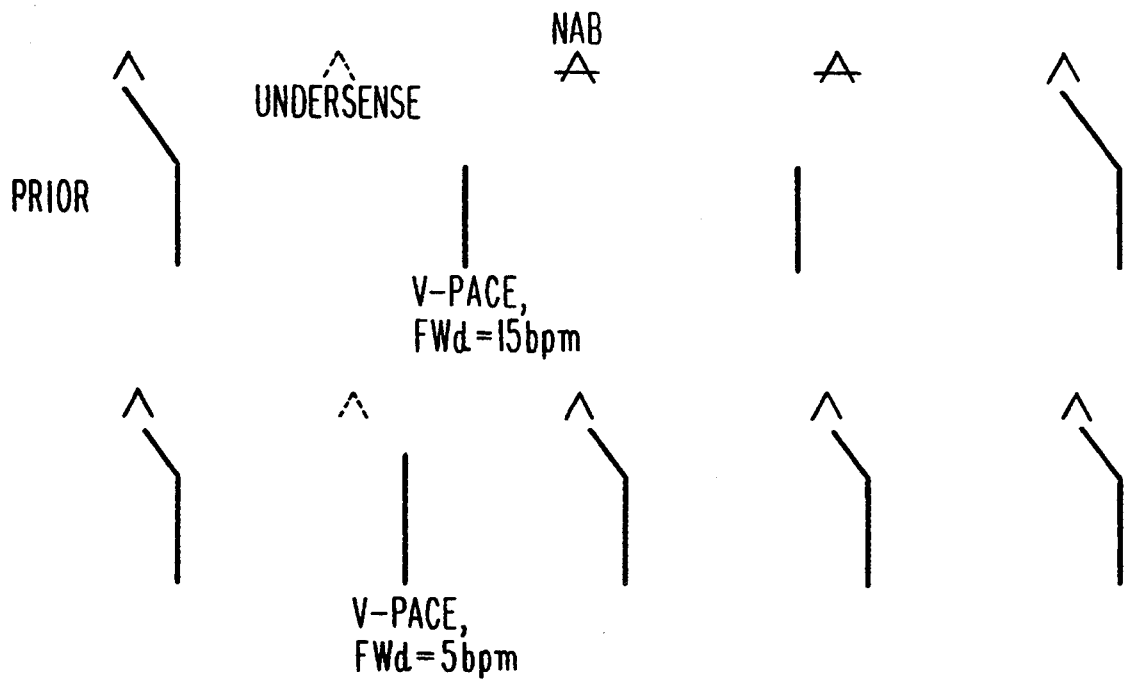
FIG. 12a is a timing diagram illustrating undersensing of a sinus beat with and without automatic adjustment of FWd.
Figure 12B:
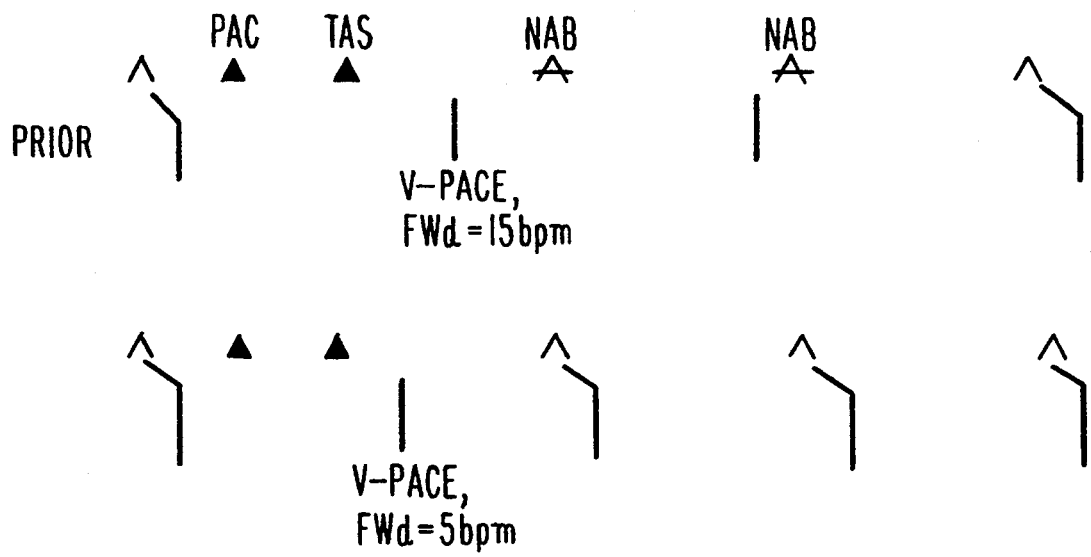
FIG. 12b is an illustration of oversensing of a sinus beat with and without the automatic FWd adjustment of this invention.

Referring now to FIGS. 12a and b, there are shown two examples of the efficacy of the auto-adjust of flywheel distance. In the timing diagram of FIG. 12a, there is shown in the top line a high sinus rate condition where there is an undersense of a sinus beat, followed by a V pace at DPL, corresponding to an FWd of about 15 bpm. The next atrial beat comes too shortly after the V pace, and is indicated as NAB (the atrial sense is blocked). There is no tracking of this beat, and the ventricular stimulus is delivered in accordance with DPL. Likewise, the next atrial beat is not tracked, and it is only until the third atrial beat after the undersense that tracking is again achieved. The second line of FIG. 12a shows the improvement resulting from minimizing FWd, e.g., adjusting it to about 5 bpm for the rate involved. Following the undersense, the V pace is delivered sooner, such that the next atrial beat is now sensed and tracking continues. Referring to FIG. 12b, there are presented two timing diagrams which illustrate the improvement with regard to oversensing, i.e., far field R wave sensing (FFRS). In the top line, where the flywheel distance is set at, e.g., 15 bpm, an FFRS is sensed and interpreted as a PAC. Consequently, the next normal atrial beat is seen as a TAS (tachycardia atrial sense), and is not tracked; the next V pace is delivered at DPL, corresponding to an FWd of 15 bpm. Following this, the next atrial sense is not tracked (NAB) and it is several more atrial beats until tracking is again achieved. As shown in the second line of FIG. 12b, improvement comes from minimizing FWd to about 5 bpm. As with the example of FIG. 12a, this permits tracking of the next sinus beat following delivery of the ventricular pace pulse.

Figure 13:
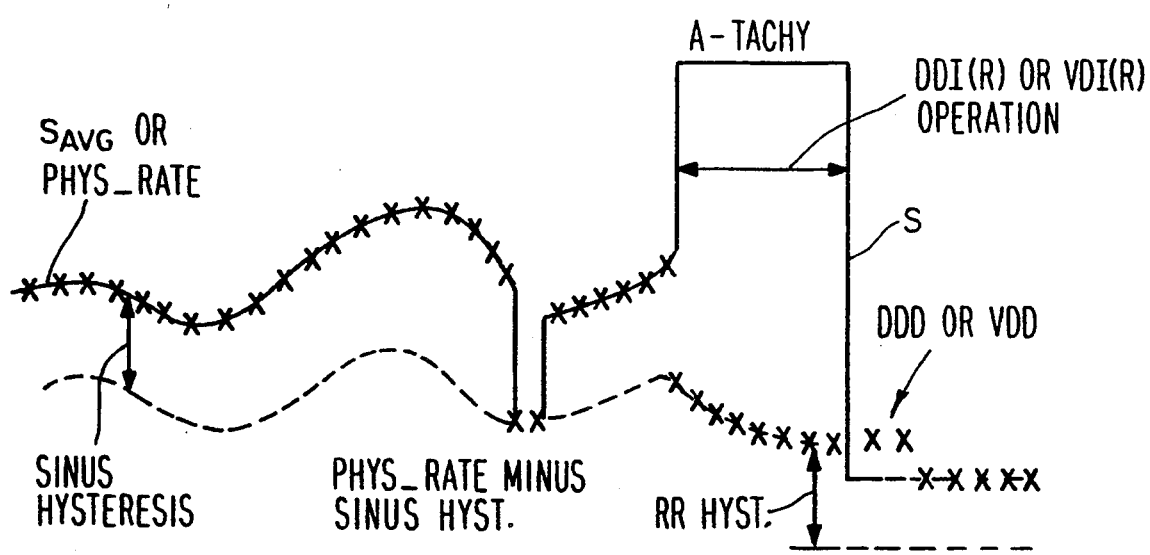
FIG. 13 is a time plot showing changes in rate with time and illustrating sensor hysteresis and flywheel hysteresis as those terms are used in this invention, and also illustrating smooth transfer to and from the different hysteresis states.

Referring now to FIG. 13, there is shown a time plot which illustrates both the sensor hysteresis and atrial (sinus) hysteresis as used in this invention, as well as the smooth transition from one mode to the other. As seen, initially there is a natural sinus rate that is being tracked, which is within the physiological range. The total atrial hysteresis (FWd plus flywheel hysteresis) is indicated as the lower dashed line which follows at a rate differential below phys-rate. There comes a time when there is an undersense of two atrial beats, resulting in pacing at physrate minus atrial hysteresis. Following this, the sinus beat is again tracked until the sinus beat rises sharply to atrial tachycardia. At this time, with the pacemaker in either DDI(R) or VDI(R) operation, the pace rate drops and the physrate is decremented downward. The pacing rate is decremented downward until it is overtaken by the sensor, such that pacing is at the RR rate. Following termination of the atrial tachycardia, for a VDD pacemaker, the pacemaker senses reappearing natural sinus beats found within the sensor hysteresis band below the RR rate, which are then tracked. For a DDD pacemaker, the re-appearing sinus beats can also be found and tracked if a hysteresis search is undertaken, i.e., pacing rate is dropped to RR—RR Hyst.

Figure 14:
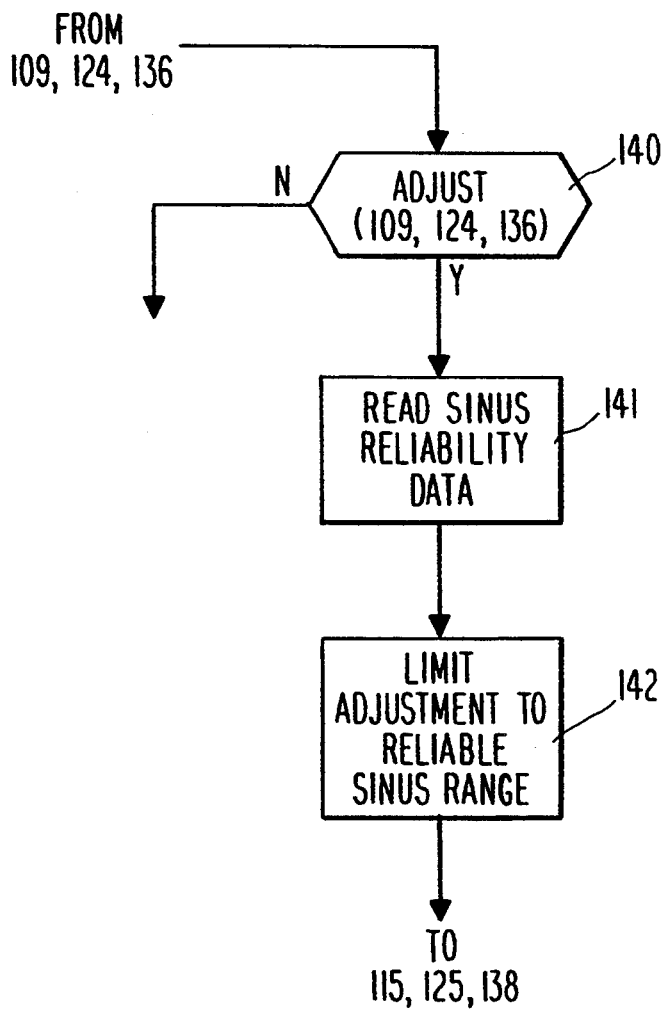
FIG. 14 is a flow diagram of a subroutine for limiting adjustment of slope, sensor hysteresis, or flywheel distance depending on data representative of sinus reliability throughout the rate range.

Referring now to FIG. 14, there is shown a software subroutine for limiting the adjustment of slope, sensor hysteresis, or flywheel distance as function of sinus reliability data. In other words, particularly for a VDD pacemaker, if it is known that the sinus is reliable only through a given rate sub range and relatively unreliable through the remainder of the rate range, it follows that automatic adjustments based on the sinus rate should not be made through the unreliable portion of the range. This information can be determined by the physician and programmed into the pacemaker, or it can be acquired automatically by the pacemaker by analyzing the stability of the sinus rate through different rate portions, or bins. Thus, for example, for a rate range between LRL of about 70 bpm and URL of about 150 bpm, the range may be divided into approximately eight subranges, or bins. For each sub-range, the sinus data may be deemed to be reliable, or non-reliable. In the subroutine of FIG. 14, for each of the auto-adjust routines of FIGS. 7, 9 and 11, the adjust decision is first made at block 140 (representing the respective adjust decision made at 109, 124 or 136). If the decision is to adjust, then at block 141 the pacemaker reads the sinus reliability data. For each sub-range where the sinus data is deemed reliable, the adjustment is permitted; for each sub-range where the sinus data is not reliable, the adjustment is prohibited, as set forth at block 142. Following this, the routine exits either to block 115, 125 or 138, to make the respective adjustments.

Going to FIG. 15, there is shown a simplified flow diagram illustrating how and when the pacemaker of this invention utilizes the different hysteresis functions. Before discussing the details of FIG. 15, the pertinent concepts and features are summarized. There is provided a first, or atrial hysteresis, which can be used following a sensed atrial signal. This first hysteresis gives a FW Hyst rate, (FW Hyst—rate=phys rate—FWd—FW Hyst), where FWd is preferably an adjustable function of rate. A second, or sensor hysteresis (RR Hyst) is utilized to modify when the sensor can overtake the atrial sense; RR Hyst rate=RR—RR Hyst, where RR Hyst can be adjustable as a function of rate. There is thus provided a capability of applying a particular hysteresis rate each cycle, depending on whether the calculated pacing interval is to be based on the flywheel rate or on sensor rate. The atrial type of hysteresis, or flywheel hysteresis rate, is normally selected for calculation of escape interval following a tracked atrial sense (AS), and when sensor rate (RR) is relatively low compared to the flywheel rate. When phys rate - FWd (i.e., DPL) is at the lower rate limit (LRL), a predetermined value of hysteresis may be utilized. The sensor hysteresis may be employed to prevent premature sensor overtaking of sinus, by requiring that RR exceed the sensed atrial rate by RR Hyst. Also, sensor hysteresis can be used in a DDD mode to interrupt pacing at sensor rate and search at RR Hyst-rate to try to find a natural sinus beat in the range RR Hyst below the RR-rate. Note that in VDD mode, "searching" is not done; rather the pacemaker keeps pacing at RR-rate, but monitors AS intervals to find sinus beats within the RR Hyst band, which beats can then be tracked as long as their rate stays above RR Hyst-rate.

Referring now to FIG. 15, at 150 it is determined whether an AS has been tracked. If yes, the routine goes to block 152, and prepares the escape interval for the next cycle by selecting the greater of FW Hyst-rate and RR-Hyst rate. Thus, if FW Hyst-rate is the greater of the two, the escape interval is set corresponding to the FW Hyst-rate for the phys-rate (or $S_{avg}$) of the last cycle. Following this, the routine goes to block 154 and waits for the next event.

If, at 150, it is determined that there had been no tracked AS, the routine branches to block 156 where it is determined whether FW-rate (corresponding to DPL) is greater than sensor rate (RR). If yes, the next pace pulse is delivered at an escape interval corresponding to the flywheel rate, where FW—rate=phys-rate-FWd. Thus, at block 158, the escape interval is set corresponding to FW-rate. After this, it is determined at block 160, whether the pacemaker is to search by dropping the pacing rate. When the pacer is to search is a decision that can be pre-programmed, or determined by an analysis of historical data. For example, the pacemaker can be programmed to search only when it has reached LRL, and no search has been conducted for a given time or a given number of cycles. If there is to be a search, the routine branches to block 166, and sets the escape interval corresponding to the greater of the 2 hysteresis rate, i.e., FW Hyst rate or RR Hyst-rate.

Returning to block 156, if it is determined that sensor rate is greater than or equal to FW-rate, then the routine goes to 162 and sets the escape interval corresponding to sensor rate (RR). Then, at 164, it is determined whether the pacemaker is to search, and if yes the escape rate is set to the greater of FW-Hyst-rate and RR Hyst rate, as seen at 166. The pacer then waits for the next event.

What is claimed is:

1. A dual chamber cyclically operating rate responsive pacemaker, having generator means for generating pace pulses for delivery to a patient's heart, atrial sense means for sensing atrial signals from said patient's atrium, ventricular sense means for sensing ventricular signals from said patient's ventricle, RR means for cyclically developing sensor-indicated pacing rate signals (RR signals) over a range of rates as a curvilinear function of at least one sensed body parameter, pace control means for controlling generation of pace pulses by said generator means in the absence of sensed heart signals, said pace control means having RR adjusting means for adjusting the rate of generated pace pulses in accordance with said RR signals, characterized by:

atrial rate means for determining a measure of atrial rate corresponding to respective sensed atrial signals within said range, determining means for determining data representative of the relation of said RR signals to corresponding values of said measure of atrial rate, and storing means for storing said data, and function adjusting means for adjusting said curvilinear function over said range of rates in accordance with said stored data.

2. The pacemaker as described in claim 1, wherein said determining means further comprises difference means for obtaining data representative of the difference between the RR signals and the measure of atrial rate (RR - $S_{avg}$) for respective cycles of operation of said pacemaker.

3. The pacemaker as described in claim 2, wherein said function adjusting means adjusts said curvilinear function at each of several predetermined rates in a manner so as to decrease said differences.

4. The pacemaker as described in claim 2, wherein said function adjusting means comprises means for storing adjustment threshold criteria, and comparison means for comparing said difference data with said criteria.

5. The pacemaker as described in claim 1, comprising means for defining sub-ranges of said range of rates, and wherein said determining means accumulates said representative data separately for each of said sub-ranges.

6. The pacemaker as described in claim 5, wherein said function adjusting means has means for periodically adjusting said function according to the data for at least one of said subranges.

7. The pacemaker as described in claim 1, said pacemaker being a dual chamber pacemaker, said generator means comprising atrial control means for controlling said generator means to generate atrial pace pulses for delivery to a patient's atrium and ventricular control means for controlling said generator means to generate pace pulses for delivery to said patient's ventricle, said pace control means also having means for controlling the generation of ventricular pace pulses in timed relation to sensed atrial signals.

8. The pacemaker as described in claim 1, comprising timer means for timing the accumulation of data, and for initiating said function adjusting means to adjust said curvilinear function following said time out.

9. The pacemaker as described in claim 1, wherein said function adjusting means comprises adjustment limit means for limiting said adjustment to a predetermined incremental change at each of a plurality of predetermined rates within said range of rates.

10. The pacemaker as described in claim 1, wherein said atrial rate means determines a value of $S_{avg}$ each time there is an atrial sense, and said determining means determines an accumulated value of the average RR-$S_{avg}$ for a predetermined sub-range of values of $S_{avg}$.

11. A dual chamber cyclically operating rate responsive pacemaker, having generator means for generating pace pulses for delivery to a patient's heart, atrial sense means for sensing atrial signals from said patient's atrium, sensor means for sensing signals indicative of desired pacing rate, RR means for cyclically developing sensor-indicated pacing rate signals (RR signals) over a range of rates as a curvilinear function of at least one sensed body parameter, pace control means for controlling generation of pace pulses by said generator means in the absence of sensed heart signals, said pace control means having RR control means for controlling the rate of generated pace pulses at an RR rate in accordance with said RR signals, comprising:

atrial rate means for determining a measure of atrial rate corresponding to respective sensed atrial signals, hysteresis means for determining a sensor hysteresis value (RR Hyst), determining means for determining data representative of corresponding values of said RR signals and said measure, and means for accumulating and storing said representative data, hysteresis adjusting means for adjusting said sensor hysteresis function in accord with said accumulated data, and said RR control means having sensor hysteresis control means for controlling rate in accord with said sensor hysteresis value.

12. The pacemaker as described in claim 11, wherein said RR control means has means for adjusting the rate to a sensor hysteresis rate equal to the RR rate minus the sensor hysteresis value (rate=RR−RR Hyst).

13. The pacemaker as described in claim 11, wherein said RR Hyst is a function of pacing rate.

14. The pacemaker as described in claim 11, comprising reliability means for storing reliability data representative of sinus rate reliability over the pacing rate range, and limit means for limiting said hysteresis adjusting means to adjust said RR Hyst as an additional function of said reliability data.

15. The pacemaker as described in claim 14, comprising sinus stability means for determining when said atrial signals are stable, and second limit means for limiting said accumulating means to accumulate said representative data as a function of said stability determination.

16. The pacemaker as described in claim 11, wherein said determining means comprises difference means for determining the difference between said RR signals and said measure of atrial rate for each said RR signal (RR − $S_{avg}$).

17. The pacemaker as described in claim 16, comprising comparing means for comparing said difference data with predetermined threshold data.

18. The pacemaker as described in claim 11, comprising comparing means for comparing said stored data with said curvilinear function, and wherein said hysteresis adjusting means comprises means for adjusting said curvilinear function in accordance with said comparison.

19. A dual chamber rate responsive pacemaker system, having generator means for generating pace pulses for delivery at least to a patient's ventricle, atrial sense means for sensing atrial signals from said patient's atrium, atrial rate means for determining the rates of said atrial signals, sensor means for sensing signals indicative of desired pacing rate for the patient, RR means for developing pacing rate (RR) signals from said sensor signals for controlling generation of pace pulses at an RR rate, atrial tracking means for controlling generation of ventricular pace pulses by said generator means in track relation to sensed atrial signals subject to predetermined conditions, RR control means for controlling the rate of generation of pace pulses in accordance with said RR signals, further comprising sensor hysteresis means for setting a sensor hysteresis (RR Hyst) value, sensor hysteresis rate means for determining a sensor hysteresis rate representative of RR rate minus RR Hyst, and said RR control means comprising sensor hysteresis rate means for controlling pacing rate to be said sensor hysteresis rate.

20. The pacemaker as described in claim 19, comprising first escape rate means for determining a first escape rate as a function of the last determined atrial rate, and escape interval selection means operative after a tracked atrial signal in the prior pacemaker cycle for selecting the escape interval of the next pacemaker cycle to correspond to the greater of said first escape rate and said sensor hysteresis rate.

21. The pacemaker system as described in claim 20, comprising a DDDR pacemaker, said generator means comprising means for generating atrial pace pulses for delivery to the patient's atrium, and ventricular pace pulses for delivery to the patient's ventricle, and wherein said escape interval selection means selects the escape interval for delivery of a next atrial pace pulse.

22. The pacemaker system as described in claim 20, comprising a VDDR pacemaker, said generator means comprising means for generating ventricular pace pulses for delivery to the patient's ventricle, and wherein said escape interval selection means selects the escape interval for tracking of a next sensed atrial signal.

23. The pacemaker system as described in claim 19, wherein said hysteresis means determines said sensor hysteresis value as a function of said RR rate.

24. A dual chamber rate responsive pacemaker system, having generator means for generating pace pulses for delivery at least to a patient's ventricle, atrial sense means for sensing atrial signals from said patient's atrium, atrial rate means for determining the rates of said atrial signals, sensor means for sensing signals indicative of desired pacing rate for the patient, RR means for developing pacing rate (RR) signals from said sensor signals for controlling generation of pace pulses at an RR rate, atrial tracking means for controlling generation of ventricular pace pulses by said generator means in track relation to sensed atrial signals subject to predetermined conditions, RR control means for controlling the rate of generation of pace pulses in accordance with said RR signals, further comprising first means for determining a first atrial hysteresis rate which is less than said atrial rate, second means for determining a sensor hysteresis rate which is less than said RR rate, and selection means operative each pacemaker cycle for enabling selection of an escape interval corresponding to one of said atrial hysteresis rate and RR hysteresis rate.

25. The pacemaker as described in claim 24, wherein said selecting means comprises means operative following a tracked atrial sense for selecting an escape interval corresponding to the larger of said atrial hysteresis rate and said sensor hysteresis rate.

26. The pacemaker as described in claim 24, comprising means operative following a prior cycle with no tracked atrial sense for setting the escape interval corresponding to the greater of said atrial rate and said sensor rate.

27. A dual chamber pacemaker system having atrial sense means for sensing atrial signals from a patient's atrium, pulse generator means for generating and delivering pace pulses to at least one of the patient's atrium and ventricle, AV control means for controlling said generator means to deliver a ventricular pace pulse in timed relation to a sensed atrial signal that can be tracked, and tracking means for determining each cycle whether there was a sensed atrial signal that can be tracked, comprising control means for controlling the pacing rate of said pulse generator means, first rate means for determining a first pacing rate which is a function of atrial rate, sensor means for determining a sensor pacing rate which is a function of at least one patient parameter, said control means being further characterized by first hysteresis means for determining a first variable hysteresis rate which is lower than said first pacing rate, second hysteresis means for determining a variable sensor hysteresis rate which is lower than said sensor rate, first comparison means for comparing said first hysteresis rate and said second hysteresis rate, and second comparison means for comparing said first rate and said second rate, first rate control means responsive to an atrial sense for setting the rate of the next pulse generated by said pulse generator means as a function of said first comparison, and second rate control means responsive to the absence of a tracked atrial sense for setting the rate of the next pulse by said pulse generator means as a function of said second comparison.

28. The pacemaker as described in claim 27, wherein said first rate control means sets the rate of the next pulse to correspond to the larger of said first hysteresis rate and said second hysteresis rate.

29. The pacemaker as described in claim 27, wherein said second rate control means sets the rate of the next pulse generated by said pulse generator to correspond to the larger of said first rate and said second rate.

30. The pacemaker as described in claim 29, further comprising search means for determining whether a hysteresis search is to be selected, said control means further having means for adjusting the escape interval following the absence of a tracked atrial sense to correspond to the larger of said first hysteresis rate and said second hysteresis rate when a said search is selected.

31. A dual chamber pacemaker having atrial sense means for sensing signals from a patient's atrium, controllable pace generator means for generating pace pulses for delivery to at least the patient's ventricle, tracking means for determining each cycle whether or not there has been an atrial signal that can be tracked, and AV control means for controlling said pace generator to generate a pace pulse in timed relation to such a sensed atrial signal that can be tracked, atrial rate means for determining a measure of atrial rate from said sensed atrial signals, first rate means for determining a first pacing rate which is a function of said measure of atrial rate, sensor rate means for determining a sensor pacing rate which is a function of at least one patient body parameter, first hysteresis means for determining a first hysteresis rate which is lower than said first pacing rate, sensor hysteresis means for determining a sensor hysteresis rate which is lower than said sensor rate, rate selection means; operative following each cycle for selecting one of the group of
(a) said first pacing rate,
(b) said second pacing rate
(c) said first hysteresis rate, and
(d) said sensor hysteresis rate, for control of said generator means during the next cycle.

32. The pacemaker as described in claim 31, wherein said rate selection means comprises means for selecting one of said rates as a function of whether an atrial sense was tracked in the prior cycle.

33. The pacemaker as described in claim 32, wherein said rate selection means comprises means for selecting the higher of said first pacing rate and said sensor pacing rate when an atrial sense has been tracked in the prior cycle.

34. The pacemaker as described in claim 31, wherein said rate selection means comprises means for selecting the higher of said first rate and said sensor rate when an atrial sense has not been tracked in the prior cycle.

35. The pacemaker as described in claim 31, comprising first adjusting means for automatically adjusting said first hysteresis rate as a function of said measure of atrial rate.

36. The pacemaker as described in claim 31, comprising second adjusting means for automatically adjusting said sensor hysteresis rate as a function of said sensor rate.

37. A dual chamber pacemaker, having generator means for generating pace pulses for delivery to a patient's heart, atrial sense means for sensing atrial signals from said patient's atrium, escape interval means for controlling the escape interval for pace pulses generated by said generator means, said escape interval means having adjusting means for adjusting the said escape interval to correspond to a determined pacing rate, comprising:

atrial rate means for determining the rate (s) of sensed atrial signals, and average rate means for determining a running average ($S_{avg}$) of said sensed rates, flywheel means for determining a flywheel value FWd as a function of said running average, said adjusting means having means for determining a flywheel pacing rate as a function of said FWd value and adjusting said escape interval to correspond to said flywheel pacing rate, accumulating means for accumulating data representative of the difference between current rate and running average ($s - S_{avg}$) corresponding to respective sensed atrial signals, and FWd adjusting means for adjusting said FWd value as a function of said representative data.

38. The pacemaker as described in claim 37, wherein said adjusting means has a means for adjusting said pacing rate to correspond to a rate FWd below said running average.

39. The pacemaker as described in claim 37, comprising atrial hysteresis means for providing an atrial hysteresis value, and wherein said adjusting means comprises means for adjusting the pacing rate to equal said running average less the combination of said FWd value and said atrial hysteresis value.

40. The pacemaker as described in claim 37, wherein said pacemaker is a VDD pacemaker, said escape interval means comprising means for controlling the escape interval of ventricular pace pulses, and further comprising ventricular sense means for sensing ventricular signals from said patient's ventricle.

41. The pacemaker as described in claim 37, wherein said pacemaker is a DDD pacemaker, said escape interval means having first control means for controlling the timing of ventricular pace pulses and second control means for controlling the timing of atrial pace pulses, and further comprising ventricular sense means for sensing ventricular signals from said patient's ventricle.

42. The pacemaker as described in claim 37, further comprising RR means for developing sensor-indicated pacing rate signals (RR signals) over a rate range as a curvilinear function of a sensed patient parameter, and rate responsive control means for controlling the rate of generated pace pulses at a sensor rate (RR) in accordance with said RR signals.

43. The pacemaker as described in claim 42, further comprising comparison means for comparing said RR signals and said flywheel pacing rate, and means for selecting control of said pacing rate as a function of said comparison.

44. The pacemaker as described in claim 43, comprising sub-range means for defining sub-range portions of said rate range, wherein said accumulating means accumulates said data corresponding to separate ones of said sub-ranges.

45. The pacemaker as described in claim 44, wherein said accumulating means comprises means for accumulating a mean value of said difference (s - $S_{avg}$) for each of said sub-ranges.

46. The pacemaker as described in claim 37, limiting determining means for limiting when said FWd adjusting means is operative to adjust said FWd value.

47. A pacemaker, having generator means for generating pace pulses for delivery to a patient's heart, atrial sense means for sensing atrial signals from said patient's atrium, ventricular sense means for sensing ventricular signals from said patient's ventricle, pace control means for controlling the escape interval of pace pulses generated by said generator means, RR means for developing sensor-indicated pacing rate signals as a curvilinear function of a sensed body parameter, and atrial rate determining means for determining the current rate of sensed atrial signals, said pace control means further comprising:

atrial hysteresis means for setting said pacing escape interval to correspond to said determined atrial rate less an atrial rate hysteresis increment, following a sensed atrial signal, and sensor hysteresis means for setting said escape interval to correspond to said RR rate less a sensor rate hysteresis increment, following delivering of a pace pulse.

48. The pacemaker as described in claim 47, comprising sensor hysteresis adjusting means for adjusting said sensor rate hysteresis increment as a function of RR signals and sensed atrial signals.

49. The pacemaker as described in claim 48, comprising atrial hysteresis adjusting means for adjusting said atrial rate hysteresis increment as a function of sensed atrial signals.

50. A rate responsive dual chamber pacemaker having generator means for generating pace pulses for delivery to a patient's heart, atrial sense means for sensing atrial signals from said patient's atrium, RR means for developing sensor-indicated pacing rate signals (RR signals), and pace control means for controlling generation of pace pulses by said generator means, said pace control means having atrial rate means for controlling the escape interval and rate of generated pace pulses in accordance with sensed atrial signals and RR rate means for controlling the escape interval and rate of generated pace pulses in accordance with said RR signals, comprising:

means for obtaining data representative of corresponding RR and atrial rates, means for determining a sensor hysteresis value as a function of said representative data, difference means for obtaining the difference of the current RR rate and current atrial rate, comparison means for comparing said difference to said sensor hysteresis value, and selecting means for selecting control of pacing escape interval by said atrial rate means or said RR rate means in response to said comparison.

51. A rate responsive pacemaker having generator means for generating pace pulses for delivery to at least one chamber of a patient's heart, atrial sense means for sensing atrial signals from said patient's atrium, atrial rate means for determining the atrial rate of sensed atrial signals, RR means for developing sensor-indicating pacing rate signals (RR signals) over a rate range, and pace control means for controlling generation of pace pulses by said generator means, said pace control means having rate means for controlling the rate and corresponding escape interval of generated pace pulses in accordance with said RR signals, comprising:

means for storing reliability data representative of the patient's sinus rate reliability over said rate range, difference means for obtaining difference data over a plurality of sensed atrial beats, which difference data is indicative of the difference between RR rates and corresponding atrial rate, and adjusting means for automatically adjusting said RR rate as a function of said reliability data and said difference data.

* * * * *